(12) United States Patent
Adamczewski et al.

(10) Patent No.: US 7,198,942 B2
(45) Date of Patent: Apr. 3, 2007

(54) ACETYLCHOLINE RECEPTOR SUBUNITS

(75) Inventors: Martin Adamczewski, Köln (DE); Ulrich Ebbinghaus-Kintscher, Dortmund (DE); Christoph Methfessel, Wuppertal (DE); Thomas Schulte, Köln (DE)

(73) Assignee: Bayer CropScience LP, Monheim (DE)

( * ) Notice: Subject to any disclaimer, the term of this patent is extended or adjusted under 35 U.S.C. 154(b) by 591 days.

(21) Appl. No.: 09/941,179

(22) Filed: Aug. 27, 2001

(65) Prior Publication Data

US 2002/0146765 A1  Oct. 10, 2002

(30) Foreign Application Priority Data

Aug. 28, 2000 (DE) .................. 100 42 177

(51) Int. Cl.
*C12N 5/10* (2006.01)
*C12N 15/11* (2006.01)
*C12N 15/63* (2006.01)
*C07K 14/705* (2006.01)

(52) U.S. Cl. .................. 435/320.1; 435/325; 530/350; 536/23.5

(58) Field of Classification Search .............. 536/23.4; 530/350

See application file for complete search history.

(56) References Cited

U.S. PATENT DOCUMENTS

| | | | | |
|---|---|---|---|---|
| 5,591,590 | A | 1/1997 | Heinemann et al. | 435/7.1 |
| 5,599,709 | A | 2/1997 | Lindstrom et al. | 435/252.3 |
| 5,683,912 | A | 11/1997 | Elgoyhen et al. | 435/252.3 |
| 2002/0006657 | A1 | 1/2002 | Adamczewski et al. | 435/252.3 |

OTHER PUBLICATIONS

Neuroscience Letters, 199, (month unavailable) 1995) pp. 107-110, M. Amar, P. Thomas S. Wonnacott. G.G. Lunt, A nicotinic acetylcholine receptor subunit from insect brain forms a non-desensitising home-oligomeric nicotinic acetylcholine receptor when expressed in *Xenopous* oocytes.
FEBS, vol. 327, No. 3, Aug. 1993, pp. 284-288, M. Amar, P. Thomas C. Johnson, G.G. Lunt and S. Wonnacott, "Agonist pharmacology of the neuronal α7 nicotinic receptor expressed in *Xenopus* oocytes".
Eur. J. Neurosci., vol. 6, (month unavailable) 1994, pp. 869-875, D. Bertrand, M. Ballivet, M. Gomez, S. Bertrand, B. Phannavong and E.D. Gundelfinger. Physiological Properties of Neuronal Nicotinic Receptors Reconstituted from the Vertebrate β2 Subunit and Drosophila αSubunits.
Neurosci. Lett., 146, (month unavailable) 1992, pp. 87-90, Daniel Bertrand, Sonia Bertrand and Marc Ballivet, "Pharmacological properties of the homomeric α7 receptor".
Methods in Neuroscience, vol. 4, (month unavailable) 1991, pp. 174-193, D. Bertrand, E. Cooper, S. Valera, D. Rungger, and M. Ballivet. "Electrophysiology of Neuronal Nicotinic Acetylcholine Receptors Expressed in *Xenopus* Oocytes following Nuclear Injection of Genes or cDNAs".
J. Insect Physiol., vol. 33, (month unavailable) 1987, pp. 771-790, "Molecular Properties and Functions of Insect Acetylcholine Receptors".
J. Exp. Biol 200, (month unavailable) 1997, pp. 2685-2692, S.D. Buckingham, B. Lapied, H. Le Corronc. F. Grolleau and D.B. Sattelle, "Imidacloprid Actions on Insect Neuronal Acetylcholine Receptors".
J. Neuroscience 16, Dec. 15, 1996, pp. 7880-7891, Bruno Buisson, Murali Gopalakrishnan, Stephen P. Arneric, James P. Sullivan and Daniel Bertand. "Human α4β2 Neuronal Nicotinic Acetylcholine Receptor in HEK 293 Cells: A Patch-Clamp Study".
Quarterly Reviews of Biophysic 25, (month unavailable) 1992, pp. 395-432, Jean-Pierre Changeux, Jean-Luc Galzi, Anne Devillers-Thiery and Daniel Bertrand, "The functional archietecture of the acetylcholine nicotinic receptor explored by affinity labelling and site-directed mutagenesis".
Proc. Nat. Acad. Sci. USA 80, (month unavailable) 1983, pp. 1111-1115, Toni Claudio, Marc Ballivet. Jim Patrick and Stephen Heinemann. "Nucleotied and deduced amino acid sequences of *Torpedo californica* acetylcholine receptor γ subunit".
Viet Witzemann, Christoph Methfessel, "Pharmacology of the nicotinic acetylcholine receptor from fetal rat muscle expressed in *Xenopus* oocytes".
J. Pharmacol Exp. Therapeut, 280, (month unavailable) 1997, pp. 428-438, O. Delbono, M. Gopalakrishnan, M. Renganathan, L.M. Monteggia, M.L. Messi and J.P. Sullivan, "Activation of the Recombinant Human α7 Nicotinic Acetylcholine Receptor Significantly Raises Intracellular Free Calcium".
Proc. Natl. Acad. Sci. USA 80, (month unavailable) Apr. 1983, pp. 2067-2071, Anne Devillers-Thiery, Jerome Giraudat, Martine Bentaboulet and Jean-Pierre Changeux. "Complete mRNA coding sequence of the acetylcholine binding α-subunit of *Torpedo marmorata* acetylcholine receptor: A model for the transmembrane organization of the polypeptide chain".
Eur. of Neurosci., vol. 10, (month unavailable) 1998, pp. 879-889, Helen M. Eastham, Robert J. Lind, Jane L. Eastlake, Barry S. Clarke, Paul Towner, Stuart E. Reynolds, Adrian J. Wolstenholme and Susan Wonnacott, "Characterization of a nicotinic acetylcholine receptor from the insect *Manduca sexta*".
Eur. J. Pharmacol., 290 (month unavailable) 1995, pp. 237-246, Murali Gopalakrishan, Bruno Buisson, Edward Touma, Tony Giordano, Jeff E. Campbell, Iris C. Hu. Diana Donnelly-Roberts, Stephen P. Arneric. Daniel Bertrand and James P. Sullivan. "Stable expression and pharmacological properties of the human α7 nicotinic acetylcholine receptor".

(Continued)

*Primary Examiner*—Michael Pak
(74) *Attorney, Agent, or Firm*—Richard F. L. Henderson; Raymond J. Harmuth

(57) ABSTRACT

The invention relates to modified acetylcholine receptor subunits, to nucleic acids coding modified acetylchloine receptor subunits, and to methods for finding active ingredients for crop protection and active pharmaceutical ingredients for treating humans and/or animals.

8 Claims, 8 Drawing Sheets

OTHER PUBLICATIONS

Figure 1B:
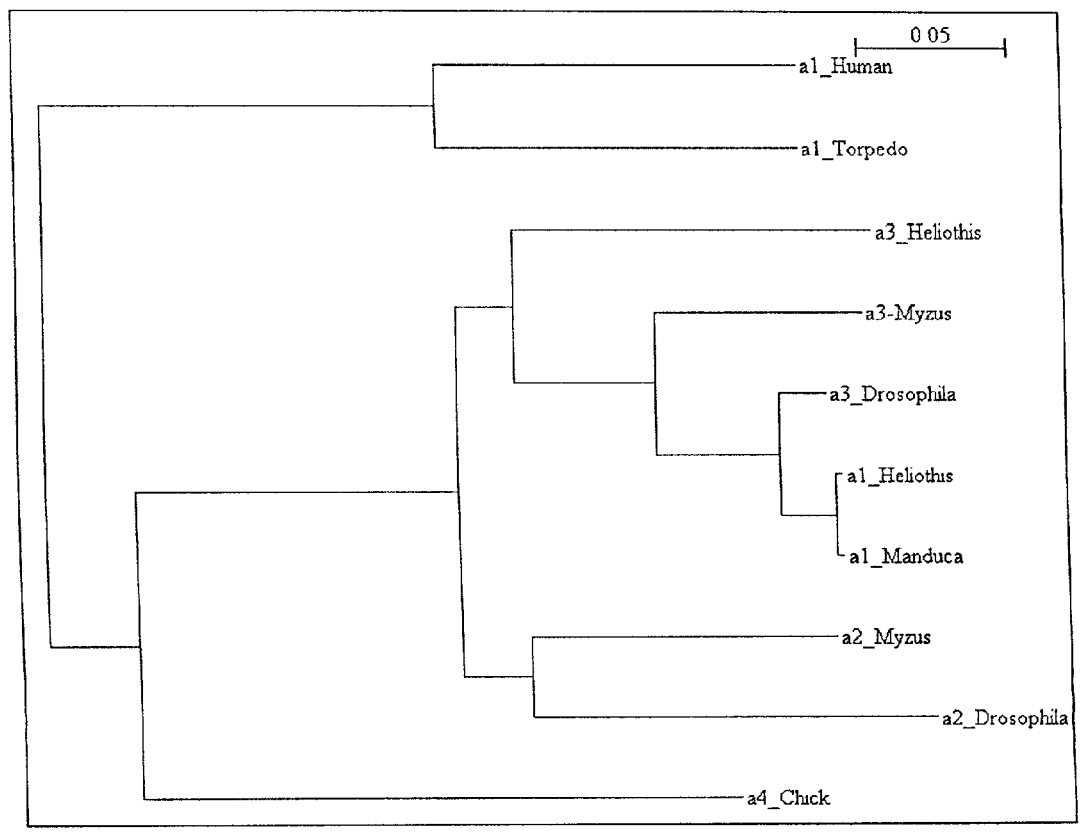

J. Pharmacol. Exp. Therapeut. 276, (month unavailable) 1996, pp. 280-297, Murali Gopalakrishnan, Lisa M. Monteggia, David J. Anderson, Eduardo J. Molinari, Marietta Piattoni-Kaplan, Diana Donnelly-Roberts, Stephen P. Arneric and James P. Sullivan, "Stable Expression, Pharmacologic Properties and Regulation of the Human Neuronal Nicotinic Acetylcholine $\alpha_4\beta_2$ Receptor".

J. Biol. Chem., 260, Mar. 1985, pp. 3440-3450, Grzegorz Grynkiewicz, Martin Poenie, and Roger Y. Tsien. "A New Generation of $Ca^{2+}$ Indicators with Greatly Improved Fluorescence Properties".

EMBO Journal, 5, (month unavailable) 1986, pp. 1503-1508, Irmgard Hermans-Borgmeyer, Dieter Zopf, Rolf-Peter Ryseck, Bernd Hovemann, Heinrich Betz and Eckart D. Gundelfinger. "Primary structure of a developmentally regulated nicotinic acetylcholine receptor protein from Drosophilia".

J. Biol. Chem. vol. 273, No. 29, Jul. 17, 1998, pp. 18394-18404, Bernhard Hermsen, Eva Stetzer, Rüdiger Thees, Reinhard Heiermann, Ulrich Ebbinghaus, Andre Schrattenholz. Axel Kretschmer, Christoph Methfessel, Sigrid Reinhard and Alfred Maelicke. "Neuronal Nicotinic Receptors in the Locust Locusta migratoria".

J. Neurochem. 73, (month unavailable) 1999, pp. 380-389, Yao Huang, Martin S. Williamson, Alan L. Devonshire, John D. Windass, Stuart J. Lansdell and Neil S. Millar. "Molecular Characterization and Imidacloprid Selectivity of Nicotinic Acetylcholine Receptor Subunits from the Peach-Potato Aphid Myzus persicae".

Biotechniques 23, Jul. 1997, Jespersen et al, pp. 48, 50 and 52, "Efficient Non-PCR-Mediated Overlap Extension of PCR Fragments by Exonuclease End Polishing".

J. Neurochem., 68, (month unavailable) 1997, pp. 1812-1819, Stuart J. Lansdell, Bertram Schmitt, Heinrich Betz, David B. Sattelle. and Neil S. Millar, "Temperature-Sensitive Expression of Drosophila Neuronal Nicotinic Acetylcholine Receptors".

Neuropharmacology, 39, (month unavailable) 2000, pp. 671-679, Stuart J. Landsdell and Neil S. Millar, "The influence of nicotinic receptor subunit composition upon against, $\alpha$-bungarotoxin and insecticide (Imidacloprid) binding affinity".

EMBO J., vol. 9, 13, (month unavailablel) 1990, pp. 4391-4398, John Marshall, Steven D. Buckingham. Ryuzo Shingai, George G. Lung, Michael W. Goosey, Mark G. Darlison, David B. Sattelle and Eric A. Barnard. "Sequence and functional expression of a single $\alpha$ subunit of an insect nicotinic acetylcholine receptor".

Br. J. Pharmacol., 123, (month unavailable) 1998, pp. 518-524, K. Matsuda, S.D. Buckingham, J.C. Freeman, M.D. Squire, H.A. Baylis and D.B. Sattelle, "Effects of the $\alpha$ subunit on imidacloprid sensitivity of recombinant nicotinic acetylcholine receptors".

Nature, vol. 299, Oct. 1982, pp. 793-797, Masaharu Noda, Hideo Takahashi, Tsutomu Tanabe. Mitsuyoshi Toyosato, Yasuji Furutani, Tadaaki Hirose, Michiko Asai, Seiichi Inayama. Takashi Miyata & Shosaku Numa, "Primary structure of $\alpha$-subunit precursor of Torpedo californica acetylcholine receptor deduced from cDNA sequence".

Nature, vol. 301, Jan. 20, 1983, pp. 251-255, Masaharu Noda, Hideo Takahashi Tsutomu Tanabe, Mitsuyoshi Toyosato, Sho Kikyotani, Tadaaki Hirose, Michiko Asai, Hideaki Takashima, Seiichi Inayama, Takashi Miyata & Shosaku Numa. Primary structures of $\beta$- and $\delta$- subunit precursors of Torpedo californica acetylcholine receptor deduced from cDNA sequences.

Nature, vol. 302, Apr. 7, 1983, pp. 528-532, Masahaur Noda, Hideo Takahaski, Tsutomu Tanabe, Mitsuyoshi Toyosato, Sho Kikyotani, Yasuji Furutani, Tadaaki Hirose, Hideaki Takashima, Selichi Inayama, Takashi Miyata & Shosaku Numa, "Structural homology of Torpedo californica acetylcholine receptor subunits".

Trends in Neuroscience 18, No. 3, (month unavailable) 1995, pp. 121-127, Marcelo O. Ortells and George G. Lunt, "Evolutionary history of the ligand-gated ion-channel superfamily or receptors".

Eur. J. Neurosci. 9, (month unavailable) 1997, pp. 480-488, D. Ragozzino, S. Fucile, A. Giovannelli, F. Grassi, A.M. Mileo, M. Ballivet, S. Alema and F. Eusebi, "Functional Properties of Neuronal Nicotinic Acetylcholine Receptor Channels Expressed in Transfected Human Cells".

EMBO J., vol. 9, No. 9, (month unavailable) 1990, pp. 2671-2677, Erich Sawruk, Patrick Schloss, Heinrich Betz and Bertram Schmitt. "Heterogeneity of Drosophila nicotinic acetylcholine receptors: SAD, a novel developmentally regulated $\alpha$-subunit".

FEBS, vol. 273, No. 1,2, Oct. 1990, Erich Sawruk, Conny Udri, Heinrich Betz and shares its genomic localization with two $\alpha$-sub-units.

EMBO J. vol. 7, No. 9, (month unavailable) 1988, pp. 2889-2894, Patrick Schloβ, Irm Hermans-Borgmeyer, Heinrich Betz and Eckart D. Gundelfinger. "Neuronal acetylcholine receptors in Drosophila: the ARD protein is a component of a high-affinity $\alpha$-bungarotoxin binding complex".

Neuron, vol. 5, Jul. 1990, pp. 35-48, Ralf Schoepfer, William G. Conroy, Paul Whiting, Martin Core and Jon Lindstrom. "Brain $\alpha$-Bungarotoxin Binding Protein cDNAs and MAbs Reveal Subtypes of This Branch of the Ligand-Gated Ion Channel Gene Superfamily".

J. Neurochem. 71. (month unavailable) 1998, pp. 853-862 R. Schulz, E. Sawruk, C. Mülhardt, S. Bertrand. A. Baumann, B. Phannavong, H. Betz, D. Bertrand, E.D. Gundelfinger and B. Schmitt. D$\alpha$3, a New Functional $\alpha$ Subunit of Nicotinic Acetylcholine Receptors from Drosophila.

J. Neurochem. 74, (month unavailable) 2000, pp. 2537-2546, Regine Schulz, Sonia Bertrand. Kathrin Chamaon, Karl-Heinz Smalla, Eckart D. Gundelfinger, and Daniel Bertrand, "Neuronal Nicotinic Acetylcholine Receptors from Drosophila: Two Different Types of $\alpha$ Subunits Coassemble Within the Same Receptor Complex".

J. Neurochem. 71, (month unavailable) 1998, pp. 903-912, F. Sgard, S.P. Fraser, M.J. Katkowska, M.B.A. Djamgoz, S.J. Dunbar, and J.D. Windass, "Cloning and Functional Characterisation of Two Novel Nicotinic Acetylcholine Receptor $\alpha$ Subunits from the Insect Pest Myus persicae".

J. Pharmacol. Exp. Therapeut. 284 (month unavailable) 1998, pp. 777-789, Kenneth A. Stauderman, L. Scott Mahaffy, Michael Akong, Gönül Velicelebi, Laura E. Chavez-Noriega, James H. Orona, Edwin C. Johnson, Kathryn J. Elliott. Alison Gillespie, Richard T. Reid, Pamala Adams, Michael M. Harpold and Janis Corney-Naeve. "Characterization of Human Recombinant Neuronal Nicotinic Acetylcholine Receptor Subunit Combinations $\alpha2\beta4$, $\alpha3\beta4$ and $\alpha4\beta4$ Stably Expressed in HEK293 Cells".

FEBS Lett., 397 (month unavailable) 1996, pp. 39-44, Eva Stetzer, Ullrich Ebbinghaus, Alexander Storch, Livia Poteur, Andre Schrattenholz, Gert Kramer, Christoph Methfessel, Alfred Maelicke. "Stable expression in HEK-293 cells of the rat $\alpha3/\beta4$ subtype of neuronal nicotinic acetylcholine receptor".

Nucleic Acids Research, vol. 25, No. 24, (month unavailable) 1997, pp. 4876-4882, Julie D. Thompson, Toby J. Gibson. Frédéric Plewniak, Francois Jeanmougin and Desmond G. Higgins, "The CLUSTAL_X windows interface: flexible strategies for multiple sequence alignment aided by quality analysis tools".

Mol. Pharmacol. 55, (month unavailable) 1999, pp. 970-981, J. Zhang, Y. Xiao G. Abdrakhmanova, W. Wang, L. Cleemann, K.J. Kellar, and M. Morad. "Activation and $Ca_{2+}$Permeation of Stably Transfected $\alpha3/\beta4$ Neuronal Nicotinin Acetylcholine Receptor".

Van De Beukel I. et al.: "Nicotinic acetylcholine receptor chimeras of rat alpha7 and Drosophila" Pesticide Science, Bd. 55, No. 10, Oct. 1999, Seiten 1031-1033, XP002198050 Seite 1032, Spalte 1, Absatz 2—Spalte 2, Absatz 2.

Database Trembl Online! Accession No. 046134, Jun. 1, 1998 Hermsen B. et al.: "Nicotinic Acetylcholine Receptor, Alpha3 Subunit (Fragment)" XP002198052 Zusammenfassung.

Database Trembl Online! Accession No. 046128, Jun. 1, 1998 Jafarigorzini S. et al.: "Nicotinic Acetylcholine Receptor Alpha 1 Subunit Precursor" XP002198053.

Butler D.H. et al.: "Mouse-Torpedo chimeric alpha-subunit used to probe channel-gating determinants on the nicotinic acetylcholine receptor primary sequence" Cellular and Molecular Neurobiology. Bd. 17, No. 1, Feb. 1997, Seiten 13-33, XP001040498 Abbildung 2: Tabelle 1.

Itier V et al: "Neuronal nicotinic receptors: from protein structure to function" Feb Letters, Elsevier Science Publishers, Amsterdam, NL. Bd. 504 Nr. 3, Aug. 31, 2001, Seiten 118-125, XP004304265 ISSN: 0014-5793 das ganze Dokument.

Figure 1A

Sequence comparison in the region of the ligand binding domain of nicotinic acetylcholine receptor α subunits Accession Numbers of α subunits used:

>gi 871037 : a4_chick
>gi|213218 : a1_Torpedo
>S77094 : a1_Human
>P17644 : a2_Drosophila
>CAA75688 : a3_Drosophila
>CAA04056 : a1_Heliothis
>AAD09808 : a2_Heliothis
>AAD09809 : a3_Heliothis
>CAA57477 : a2_Myzus
>AJ236786 : a3_Myzus Parameters of ClustalX 1.81(Thompson et al. 1997, IGBMC, Strasbourg, France)

-type=protein \
-pwmatrix=gonnet \
-pwgapopen=10.00 \
-pwgapext=0.10 \
-matrix=gonnet \
-gapopen=10.00 \
-gapext=0.20 \
-maxdiv=30 \
-endgaps \
-novgap \
-hgapresidues=GPSNDQEKR \
-gapdist=4 \

```
a3_Heliothis    YDDLLSNYNR  LIRPVTNVSD  ILTVRLGLKL  SQLMEVNLKN  QVMTTNLWVE
a2_Myzus        YDDLLSNYNR  LIRPVGNNSD  RLTVKMGLKL  SQIIEVNLRN  QIMTTNVWVE
a2_Drosophila   YDDLLSNYNR  LIRPVSNNTD  TVLVKLGLRL  SQLIDLNLKD  QILTTNVWLE
a1_Manduca      YDDLLSNYNK  LVRPVLNVSD  ALTVRIKLKL  SQLIDVNLKN  QIMTTNLWVE
a1_Heliothis    YDDLLSNYNK  LVRPVLNVSD  ALTVRIKLKL  SQLIDVNLKN  QIMTTNLWVE
a3_Drosophila   YDDLLSNYNK  LVRPVVNVTD  ALTVRIKLKL  SQLIDVNLKN  QIMTTNLWVE
a3_Myzus        YDDLLSNYNK  LVRPVLNNTD  PLPVRIKLKL  SQLIDINLKN  QIMTTNLWVE
a1_Torpedo      VANLLENYNK  VIRPVEHHTH  FVDITVGLQL  IQLISVDEVN  QIVETNVRLR
a1_Human        VAKLFKDYSS  VVRPVEDHRQ  VVEVTVGLQL  IQLINVDEVN  QIVTTNVRLK
```

Figure 1A (cont(d))

```
a4_Chick        LKKLFSGYNK WSRPVANISD VVLVRFGLSI AQLIDVDEKN QMMTTNVWVK a3_Heliothis    Q.........  ..........  ......KWFD YKLQWNPDDY GGVEMLYVPS
a2_Myzus        Q.........  ..........  ......EWND YKLKWNPEDY GGVDTLHVPS
a2_Drosophila   H.........  ..........  ......EWQD HKFKWDPSEY GGVTELYVPS
a1_Manduca      Q.........  ..........  ......SWYD YKLSWEPREY GGVEMLHVPS
a1_Heliothis    Q.........  ..........  ......SWYD YKLSWEPREY GGVEMLHVPS
a3_Drosophila   Q.........  ..........  ......SWYD YKLKWEPKEY GGVEMLHVPS
a3_Myzus        Q.........  ..........  ......YWYD YKLTWNPDEY GGVEGLHVPS
a1_Torpedo      Q.........  ..........  ......QWID VRLRWNPADY GGIKKIRLPS
a1_Human        QGDMVDLPRP SCVTLGVPLF SHLQNEQWVD YNLKWNPDDY GGVKKIHIPS
a4_Chick        Q.........  ..........  ......EWHD YKLRWDPQEY ENVTSIRIPS ------------------------------------------------------
a3_Heliothis    EHIWLPDIVL YNNWDGNYEV TLMTKATLKY TGEVNWKPPA IYKSSCEINV
a2_Myzus        EHIWLPDIVL YNNADGNYEV TIMTKAILHY TGKVVWKPPA IYKSFCEINV
a2_Drosophila   EHIWLPDIVL YNNADGEYVV TTMTKAILHY TGKVVWTPPA IFKSSCEIDV
a1_Manduca      DHIWRPDIVL YNNADGNFEV TLATKATLNY TGRVEWRPPA IYKSSCEIDV
a1_Heliothis    DHIWRPDIVL YNNADGNFEV TLATKATLNY TGRVEWRPPA IYKSSCEIDV
a3_Drosophila   DHIWRPDIVL YNNADGNFEV TLATKATLNY TGRVEWRPPA IYKSSCEIDV
a3_Myzus        EHVWRPDIVL YNNADGNFEV TLATKAMLHY SGRVEWKPPA IYKSSCEIDV
a1_Torpedo      DDVWLPDLVL YNNADGDFAI VHMTKLLLDY TGKIMWTPPA IFKSYCEIIV
a1_Human        EKIWRPDLVL YNNADGDFAI VKFTKVLLQY TGHITWTPPA IFKSYCEIIV
a4_Chick        ELIWRPDIVL YNNADGDFAV THLTKAHLFY DGRIKWMPPA IYKSSCSIDV ------------           --------------------
a3_Heliothis    EYFPFDEQTC FMKFGSWTYN GAQVDLKHMD QSPGSS.LVH VGIDLSEFYL
a2_Myzus        EYFPFDEQTC SMKFGSWTYD GYMMDLRHIS QAPDSD.VIE VGIDLQDYYL
a2_Drosophila   RYFPFDQQTC EMKFGSWTYD GDQIDLKHIS QKNDKDNKVE IGIDLREYYP
a1_Manduca      EYFPFDQQTC VMKFGSWTYD GFQVDLRHID EVRGTN.VVE LGVDLSEFYT
a1_Heliothis    EYFPFDQQTC VMKFGSWTYD GFQVDLRHID EARGTN.VVE LGVDLSEFYT
a3_Drosophila   EYFPFDEQTC VMKFGSWTYD GFQVDLRHID ELNGTN.VVE VGVDLSEFYT
a3_Myzus        EFFPFDEQTC VMKFGSWTYD GFQVDLRHAN EVSGSR.VVD VGVDLSEFYA
a1_Torpedo      THFPFDQQNC TMKLGIWTYD GTKVSISPES DR........ ..PDLSTFME
a1_Human        THFPFDEQNC SMKLGTWTYD GSVVAINPES DQ........ ..PDLSNFME
a4_Chick        TFFPFDQQNC KMKFGSWTYD KAKIDLVSMH SH........ ..VDQLDYWE

***********************************
a3_Heliothis    SVEWDILEVP ATRNEEYYPC CPEP.FSDIT FKLTMRRKTL FYTVNLIIPC
a2_Myzus        SVEWDIMGVP AVRHEKFYVC CEEP.YLDIF FNITLRRKTL FYTVNLIIPC
a2_Drosophila   SVEWDILGVP AERHEKYYPC CAEP.YPDIF FNITLRRKTL FYTVNLIIPC
a1_Manduca      SVEWDILEVP AVRNEKFYTC CDEP.YLDIT FNITMRRKTL FYTVNLIIPC
a1_Heliothis    SVEWDILEVP AVRNEKFYTC CDEP.YLDIT FNITMRRKTL FYTVNLIIPC
a3_Drosophila   SVEWDILEVP AVRNEKFYTC CDEP.YLDIT FNITMRRKTL FYTVNLIIPC
a3_Myzus        SVEWDILEVP AIRNEKYYTC CEEP.YLDIT FNITMRRKTL FYTVNLIIPC
a1_Torpedo      SGEWVMKDYR GWKHWVYYTC CPDTPYLDIT YHFIMQRIPL YFVVNVIIPC
a1_Human        SGEWVIKESR GWKHSVTYSC CPDTPYLDIT YHFVMQRLPL YFIVNVIIPC
a4_Chick        SGEWVIINAV GNYNSKKYEC CTEI.YPDIT YSFIIRRLPL FYTINLIIPC
```

Relationship of nicotinic acetylcholine receptor α subunit sequences based on comparison of their ligand binding domains Tree of amino acid sequences from Fig. 1A produced from alignment of amino acid sequences from Fig. 1A by the program njplotwin95 using standard parameters.

2A) Receptor comprising polypeptide according to SEQ ID NO: 3 and chicken α2

Figure 2:
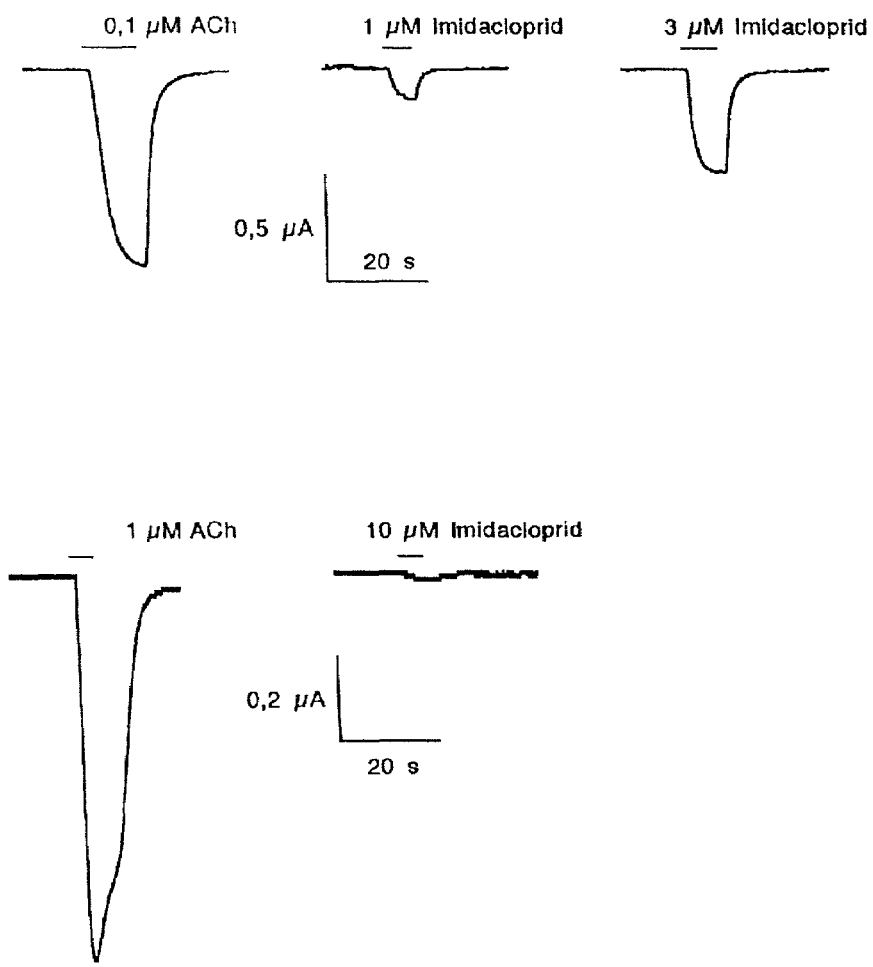

Figure 2 (cont(d))
2B) Receptor comprising chicken α4 and chicken α2
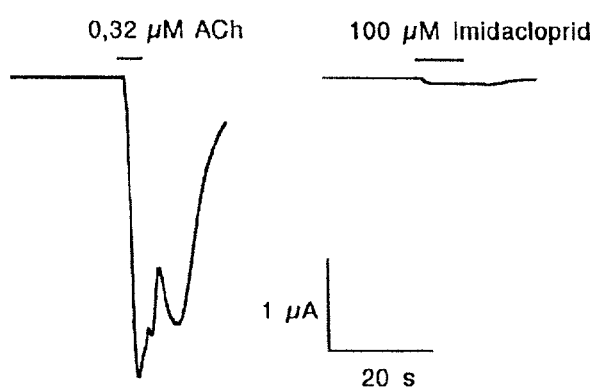
2C) Receptor comprising Heliothis α1 and chicken β2
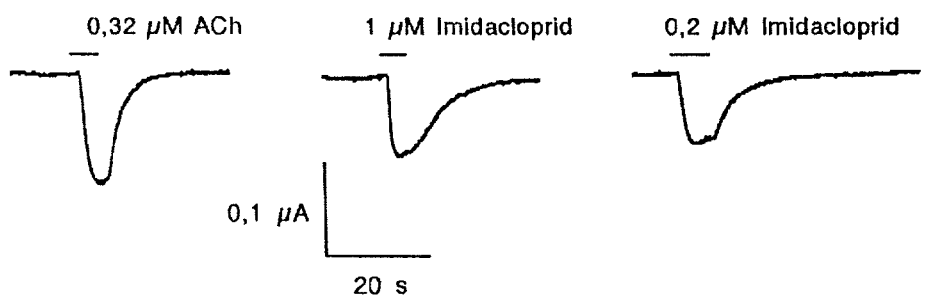

Figure 2 (cont(d))
2D) Receptor comprising polypeptide according to SEQ ID NO: 7 and chicken β2
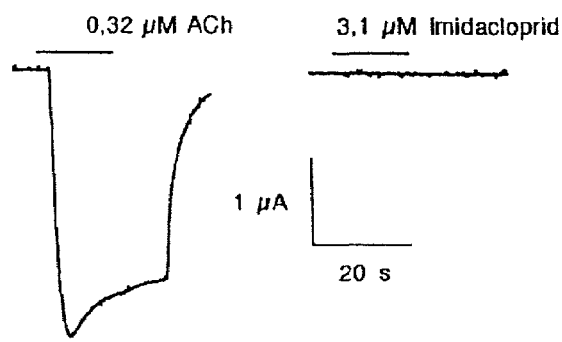
2E) Receptor comprising polypeptide according to SEQ ID NO: 11 and chicken β2
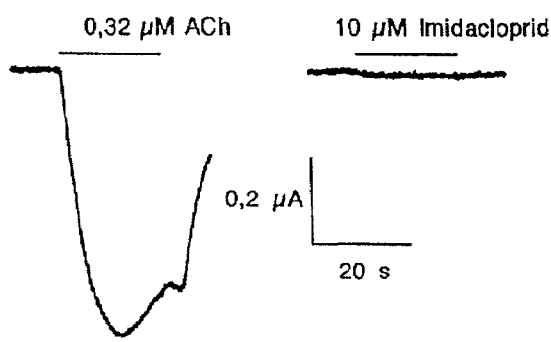

A: Receptor comprising chicken α-4 and chicken α-2 expressed in Sf-9 cells
B: Receptor comprising polypeptide according to SEQ ID NO: 3 and chicken α-2 expressed in Sf-9 cells

ACETYLCHOLINE RECEPTOR SUBUNITS

FIELD OF THE INVENTION

The invention relates to modified acetylcholine receptor subunits, to nucleic acids coding therefor, and to a method for finding active ingredients for crop protection and active pharmaceutical ingredients for treating humans and/or animals.

BACKGROUND OF THE INVENTION

Nicotinic acetylcholine receptors are ligand-gated ion channels which play a part in neurotransmission in the animal kingdom. The binding of acetylcholine or other agonists to the receptor causes a transient opening of the channel and allows cations to flow through. It is assumed that a receptor consists of five subunits grouped around a pore. Each of these subunits is a protein consisting of an extracellular N-terminal part followed by three transmembrane regions, an intracellular part, and a fourth transmembrane region and a short extracellular C-terminal part. Certain subunits carry on their extracellular part the binding site for ligands such as acetylcholine. Two vicinal cysteines form part of this binding site and are therefore a structural feature common to all ligand-binding subunits, which are also referred to as $\alpha$ subunits. Subunits without this structural feature are referred to, depending on the localization and function of the receptor, as $\beta$, $\gamma$, $\delta$ or $\epsilon$ subunits (Changeux et al. 1992).

Acetylcholine receptors have been particularly well investigated in vertebrates. Three groups can be distinguished on the basis of their anatomical localization and their functional properties (conduction properties of the channel, desensitization, sensitivity to agonists and antagonists and to toxins such as, for example, $\alpha$-bungarotoxin). The classification correlates with the molecular composition of the receptors. They are heterooligomeric receptors with the subunit composition $\alpha_2\beta\gamma\delta$, which occur in muscle (Noda et al. 1982, Claudio et al. 1983, Devillers-Thiery et al. 1983, Noda et al. 1983a, b), heterooligomeric receptors which contain subunits from the $\alpha2$–$\alpha6$ and $\beta2$–$\beta4$ group and which occur in the nervous system (Schoepfer et al. 1990, Heinemann et al. 1997) and homooligomeric receptors which contain subunits from the $\alpha7$–$\alpha9$ group and which likewise occur in the nervous system (Lindstrom et al. 1997, Elgoyhen et al. 1997). This classification is also supported by the relationship of the gene sequences of the various subunits. The sequences of functionally homologous subunits from different species are typically more similar than sequences of subunits from different groups but from the same species. This is illustrated with some examples in FIG. 1B. In addition, the gene sequences of all known acetylcholine receptor subunits are similar to a certain extent not only with one another but also with those of some other ligand-gated ion channels (for example the serotonin receptors of the $5HT_3$ type, the GABA-gated chloride channels, the glycine-gated chloride channels). It is therefore assumed that all these receptors are derived from a common precursor and they are assigned to a gene superfamily (Ortells et al. 1995).

In insects, acetylcholine is the most important excitatory neurotransmitter in the central nervous system. Accordingly, acetylcholine receptors can be detected electrophysiologically in preparations of central ganglia from insects. Detection is possible both at postsynaptic and presynaptic nerve endings and on the cell bodies of interneurons, motor neurons and modulatory neurons (Breer et al. 1987, Buckingham et al. 1997). Among the receptors there are some which are inhibited by $\alpha$-bungarotoxin and some which are insensitive (Schloβ et al. 1988). The acetylcholine receptors are moreover the molecular point of attack of important natural (for example nicotine) and synthetic insecticides (for example chloronicotinyls).

The gene sequences of a number of insect nicotinic acetylcholine receptors are already known. Thus, the sequences of five different subunits in *Drosophila melanogaster* have been described (Bossy et al. 1988, Hermanns-Borgmeyer et al. 1986, Sawruk et al. 1990a, 1990b, Schulz et al. 1998), likewise five in *Locusta migratoria* (Hermsen et al. 1998), one in *Schistocerca gregaria* (Marshall et al. 1990), six in *Myzus persicae* (Sgard et al. 1998, Huang et al. 1999), two sequences in *Manduca sexta* (Eastham et al. 1997, Genbank AJ007397) and six in *Heliothis virescens* (Genbank AF 096878, AF 096879, AF 096880, AF143846, AF143847, AJ 000399). In addition, a number of partial gene sequences from *Drosophila melanogaster* has been characterized as so-called expressed sequence tags (Genbank AA540687, AA698155, AA697710, AA697326). All these sequences are classified into $\alpha$ and $\beta$ subunits depending on whether the two vicinal cysteines are present in the ligand binding site or not.

Recombinant expression of insect nicotinic receptors has proved to be more difficult than that of the analogous receptors from vertebrates or *C. elegans*. Thus, it has not yet been possible to express nicotinic receptors consisting only of insect subunits in such a way that their functional properties are the same as those of natural receptors (Marshall et al. 1990, Amar et al. 1995, Hermsen et al. 1998, Sgard et al. 1998). Relevant functional properties are, for example, sensitivity to agonists and antagonists, conductance for ion currents or desensitization. However, at least some $\alpha$ subunits from various insect species contribute to a functional receptor on coexpression of a vertebrate non-$\alpha$ subunit in place of an insect $\beta$ subunit. The ligand-induced conductance of such hybrid receptors has been investigated in *Xenopus laevis* oocytes. Combinations of, for example, the *Drosophila* $\alpha1$, $\alpha2$ or $\alpha3$ subunit with the chicken or rat $\beta2$ subunit lead to receptors whose sensitivity to agonists and antagonists or whose conductance for ion currents resemble those receptors detected in native preparations (Bertrand et al. 1994, Lansdell et al. 1997, Schulz et al. 1998, 2000, Matsuda et al. 1998). On the other hand, it has to date been possible to detect the expression in cell lines of hybrid receptors consisting, for example, of combinations of the *Myzus persicae* $\alpha1$, $\alpha2$ or $\alpha3$ subunit with the rat $\beta2$ subunit or of combinations of the *Drosophila* $\alpha1$, $\alpha2$ or $\alpha3$ subunit with the rat $\beta2$ or $\beta4$ subunit only through the binding of nicotinic ligands (Lansdell et al. 1997, 2000, Huang et al. 1999). The ligand-induced conductance of such receptors has not to date been detected in any case.

A further attempt to approach the expression of insect nicotinic receptors is represented by chimeric subunits (van den Beukel 1998). Sections of the gene sequence of the *Drosophila* $\alpha2$ subunit were inserted recombinantly into the gene sequence of the rat $\alpha7$ subunit. Expression of the chimeras in *Xenopus laevis* oocytes was detectable through binding of nicotinic ligands, but these receptors did not display the ligand-induced conductance either.

SUMMARY OF THE INVENTION

It is an object of the present invention to provide modified acetylcholine receptor subunits. It is another object of the present invention to provide a methods for finding active crop protection or pharmaceutical ingredients.

According to one aspect of the invention there are provided modified acetylcholine receptor subunits comprising an a subunit of a vertebrate acetylcholine receptor having a region which is homologous with the amino acid sequence shown in SEQ ID NO: 1, wherein at least one amino acid in the region of the a subunit of the vertebrate acetylcholine receptor which is homologous with the amino acid sequence shown in SEQ ID NO: 1 is replaced by an amino acid which occurs at the identical position in the corresponding region of an a subunit of an insect acetylcholine receptor. The replacement of the at least one amino acid in the region of the α subunit results in a change of the amino acid sequence when compared the original amino acid sequence. As used herein, "the original amino acid sequence" refers to the amino acid sequence of the unmodified α subunit, that is, the α subunit the wherein no replacement has occurred.

According to other aspects of the invention there are provided DNA constructs, vectors and host cells having a nucleic acid wherein the nucleic acid contains a nucleotide sequence which codes for the modified acetylcholine receptor subunit.

Other aspects of the invention include methods for preparing the modified acetylcholine receptor subunit, and methods for finding active ingredients for crop protection or active pharmaceutical ingredients for the treatment of humans or animals.

According to a further aspect of the invention there are provided isolated acetylcholine receptors having an α subunit and a β subunit. The α subunit comprises a region having the same amino acid sequence as a region of an α subunit selected from the group consisting of the α2 subunit from *Myzus persicae*, the α3 subunit from *Myzus persicae*, α1 subunit from *Heliothis virescens*, the α1 subunit from *Manduca sexta*, and he α1, α2 or α3 subunits from *Drosophila melanogaster*.

DETAILED DESCRIPTION

The recombinant expression of insect nicotinic receptors or those nicotinic receptor constructs which correspond to insect receptors in their sensitivity to agonists and antagonists and their ligand-induced conductance for ion currents in eukaryotic cell lines is not only a scientific problem unsolved to date but also of great practical significance, for example for establishing high-throughput test systems for searching for novel active ingredients for crop protection and active pharmaceutical ingredients for the treatment of humans and/or animals.

The present invention is thus based in particular on the object of providing a test method and the constituents of a test method with which it is possible to find compounds which, as modulators, in particular as agonists or antagonists, alter the conduction properties of insect nicotinic receptors. Such compounds can be used as active ingredients for crop protection or active pharmaceutical ingredients for the treatment of humans and/or animals.

The object is achieved by providing modified acetylcholine receptor subunits where at least one amino acid in the region of an α subunit of a vertebrate acetylcholine receptor which is homologous with the amino acid sequence shown in SEQ ID NO: 1 is replaced by an amino acid which occurs at the identical position in the corresponding region of an α subunit of an insect acetylcholine receptor. The replacement leads to a change in the amino acid sequence.

As used herein "vertebrate acetylcholine receptor subunits" is intended to mean receptor subunits having amino acid sequences identical to acetylcholine receptor subunits which naturally occur in vertebrates or which are isolated from vertebrates, while "insect acetylcholine receptor subunits" is intended to mean receptor subunits having amino acid sequences identical to acetylcholine receptor subunits which naturally occur in insects or which are isolated from insects.

The similarity of regions and the correspondence of the amino acid positions of two or more receptor subunits can be established by amino acid sequence comparison using conventional methods. One conventional method comprises the use of the "Gap" or "Pileup" programs from the GCG program package version 10.0 (GCG Genetics Computer Group, Inc., Madison Wis., USA) for comparing two or more amino acid sequences. It is also possible to use the ClustalX program (version 1.81) (Thompson et al. 1997, IGBMC, Strasbourg, France) or other similar programs. The programs are used with standard settings. The sequences to be compared comprise the region from the N terminus of the protein up to the first transmembrane region.

Amino acids "occurring at the identical position" in two or more receptor subunits are defined as being those arranged in a column by the sequence comparison programs. A "homologous region" in two or more receptor subunits is likewise defined as being one arranged in a column by the sequence comparison programs.

Because of the different numbering of structurally and/or functionally corresponding regions in acetylcholine receptor subunits from different species, the α subunit of the ray *Torpedo californica* will be used as a reference standard for describing the amino acid(s) to be replaced or the region to be replaced. The amino acid sequence shown in SEQ ID NO: 1 corresponds to that region of the *Torpedo californica* α subunit which starts with the amino acid 123 and ends with the amino acid 167. The numbering has been taken from the entry "Acetylcholine Receptor Protein, Alpha Chain Precursor" in the Swissprot database (P02710).

FIG. 1A illustrates the sequence comparison, the correspondence of amino acids, and the homology of regions with sequences from some relevant subunits. FIG. 1B demonstrates that, by comparing the sequences, it is possible to group the subunits according to their function and localization and to differentiate between insect receptor subunits and vertebrate receptor subunits. The program used for this analysis was njplotwin95 from the WWW-Query program package (Perrière et al. 1996). This analysis can easily be extended to other, even as yet unknown, acetylcholine receptor subunit sequences from other species.

In the acetylcholine receptor subunits according to the invention there are preferably at least four, particularly preferably at least seven, very particularly preferably all of the amino acids in the region described above of an α subunit of a vertebrate acetylcholine receptor replaced by the corresponding number of amino acids from an α subunit of an insect acetylcholine receptor.

Such modified subunits display greater sensitivity to insecticidal active ingredients such as, for example, imidacloprid than an unmodified subunit.

The α subunits of vertebrate acetylcholine receptors are preferably mouse, rat, chicken, dog, zebra fish, rhesus monkey, bovine or porcine neuronal subunits.

The α subunits of insect acetylcholine receptors are preferably the α2 subunit or the α3 subunit of Myzus persicae, or the α1 subunit of *Heliothis virescens* or *Manduca sexta*, or the α1, α2 or α3 subunit of *Drosophila melanogaster*.

A modified acetylcholine receptor subunit with an amino acid sequence shown in SEQ ID NO: 3 is particularly preferred.

The present invention also relates to acetylcholine receptors which comprise the subunits according to the invention. As structural partners of the subunits according to the invention, these receptors preferably contain a mouse, rat, chicken, dog, zebra fish, rhesus monkey, bovine or porcine β2 subunit.

Nor is it necessary for the unmodified regions of the subunits according to the invention to be identical to the corresponding regions of naturally occurring α subunits of vertebrate acetylcholine receptors as long as it is ensured that the receptors display a ligand-induced conductance for ion currents.

Such differences may occur at various sites and more than once in an α subunit, such as, for example, on the peptide backbone, on the amino acid side chain, or at the amino and/or carboxy terminus. They comprise, for example, acetylations, acylations, ADP ribosylations, amidations, covalent linkages to flavins, haem portions, nucleotides or nucleotide derivatives, lipids or lipid derivatives or phosphatidylinositol, cyclizations, disulphide bridge formations, demethylations, cystine formations, formylations, gamma-carboxylations, glycosylations, hydroxylations, iodinations, methylations, myristoylations, oxidations, proteolytic processings, phosphorylations, selenoylations and tRNA-mediated additions of amino acids.

The subunits according to the invention may furthermore have, compared with the corresponding regions of naturally occurring acetylcholine receptor subunits, deletions or amino acid substitutions as long as they are still able to mediate the abovementioned conductance. Conservative substitutions are preferred. Such conservative substitutions comprise variations where one amino acid is replaced by another amino acid from the following group:

1. small aliphatic, nonpolar or low-polarity residues: Ala, Ser, Thr, Pro and Gly;
2. polar, negatively charged residues and their amides: Asp, Asn, Glu and Gln;
3. polar, positively charged residues: His, Arg and Lys;
4. large aliphatic, nonpolar residues: Met, Leu, Ile, Val and Cys; and
5. aromatic residues: Phe, Tyr and Trp.

The following list shows preferred conservative substitutions:

| Original residue | Substitution |
|---|---|
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |

-continued

| Original residue | Substitution |
|---|---|
| Thr | Ser |
| Trp | Tyr |
| Tyr | Trp, Phe |
| Val | Ile, Leu |

The present invention also relates to nucleic acids which code for the subunits according to the invention.

The nucleic acids according to the invention are, in particular, single-stranded or double-stranded deoxyribonucleic acids (DNA) or ribonucleic acids (RNA). Preferred embodiments are fragments of genomic DNA which may contain introns, and cDNAs.

A preferred embodiment of the nucleic acids according to the invention is represented by a cDNA which has the nucleotide sequence shown in SEQ ID NO: 2.

The present invention also relates to DNA constructs which comprise a nucleic acid according to the invention and a heterologous promoter.

The term “heterologous promoter” as used herein refers to a promoter which has properties different from that promoter which controls expression of the relevant gene in the original organism. The term “promoter” as used herein refers generally to expression control sequences.

The selection of heterologous promoters depends on whether prokaryotic or eukaryotic cells or cell-free systems are used for the expression. Examples of heterologous promoters are the early or late promoter of SV40, of adenovirus or of cytomegalovirus, the baculovirus immediate early promoter, the *Drosophila melanogaster* metallothionein promoter, the lac system, the trp system, the major operator and promoter regions of phage lambda, the control regions of the fd coat protein, the promoter of 3-phosphoglycerate kinase, the promoter of acid phosphatase and the promoter of the yeast α mating factor.

The invention also relates to vectors which contain a nucleic acid according to the invention or a DNA construct according to the invention. Vectors which can be used are all plasmids, phasmids, cosmids, YACs or artificial chromosomes used in laboratories of molecular biology.

The present invention also relates to host cells which contain a nucleic acid according to the invention, a DNA construct according to the invention or a vector according to the invention.

Suitable host cells are both prokaryotic cells such as bacteria of the genera *Bacillus, Pseudomonas, Streptomyces, Streptococcus, Staphylococcus*, preferably *E. coli*, and eukaryotic cells such as yeasts, mammalian, amphibian, insect or plant cells. Preferred eukaryotic host cells are HEK-293, Schneider S2, *Spodoptera* Sf9, CHO, COS1, COS7 cells and plant cells in cell culture.

The present invention also relates to methods for preparing the subunits according to the invention. The subunits encoded by the nucleic acids according to the invention can be prepared by cultivating host cells which contain one of the nucleic acids according to the invention under suitable conditions. It is moreover possible to adapt the nucleic acid to be expressed to the codon usage of the host cells. The desired subunits can then be isolated from the cells or the culture medium in a conventional way. The subunits can also be prepared in in vitro systems.

A rapid method for isolating the subunits according to the invention synthesized by host cells using a nucleic acid according to the invention starts with the expression of a fusion protein wherein the fusion partner can be affinity-purified in a simple manner. The fusion partner can be, for example, glutathione S-transferase. The fusion protein can then be purified on a glutathione affinity column. The fusion partner can be removed by partial proteolytic cleavage for example at linkers between the fusion partner and the subunit according to the invention to be purified. The linker can be designed so that it includes target amino acids, such as arginine and lysine residues, which define sites for trypsin cleavage. Such linkers can be generated by employing standard cloning methods using oligonucleotides.

Further preferable purification methods are based on preparative electrophoresis, FPLC, HPLC (for example with use of gel filtration, reverse phase or slightly hydrophobic columns), gel filtration, differential precipitation, ion exchange chromatography and affinity chromatography.

Since acetylcholine receptors are composed of membrane proteins, it is preferable to carry out detergent extractions in the purification methods, for example using detergents which influence the secondary and tertiary structures of the polypeptides only slightly or not at all, such as nonionic detergents.

The purification of the subunits according to the invention may comprise the isolation of membranes starting from host cells which express the nucleic acids according to the invention. Such cells preferably express the polypeptides according to the invention in an adequate copy number such that the amount of the polypeptides in a membrane fraction is at least 10 times higher than that found in comparable membranes of cells which naturally express acetylcholine receptors; the amount is particularly preferably at least 100 times, very particularly preferably at least 1000 times, higher.

The terms "isolation or purification" as used herein mean that the subunits according to the invention are separated from other proteins or other macromolecules from the cell or the tissue. A composition containing the subunits according to the invention is preferably enriched in terms of the protein content compared with a preparation from the host cells by at least 10 times and particularly preferably by at least 100 times.

Affinity purification of the subunits according to the invention is possible even without fusion partners with the aid of antibodies which bind to the polypeptides.

The present invention further relates to methods for preparing the nucleic acids according to the invention. The nucleic acids according to the invention can be prepared in a conventional way. For example, complete chemical synthesis of the nucleic acid molecules is possible. It is also possible to insert gene fragments, for example from genes for acetylcholine receptor subunits from insects, into the gene of interest, for example a gene for a vertebrate acetylcholine receptor subunit. It is possible to utilize restriction cleavage sites for this purpose, or else to create suitable restriction cleavage sites, for example by the method of site-directed mutagenesis or PCR. Finally, genes for acetylcholine receptor subunits of interest can also be modified directly by the methods of site-directed mutagenesis or PCR in order to obtain the desired properties and structural features. Homologous recombinations between DNA sequences also provides a possibility for specific modification of the genes.

Chemically synthesized oligonucleotides are employed as primers for PCR methods. The term "oligonucleotide(s)" as used herein means DNA molecules consisting of 10 to 50 nucleotides, preferably 15 to 30 nucleotides. They are chemically synthesized.

It is possible with the aid of the nucleic acids and acetylcholine receptor subunits according to the invention to identify novel active ingredients for crop protection and active pharmaceutical ingredients for the treatment of humans and animals, such as chemical compounds which, as modulators, in particular as agonists or antagonists, alter the properties of the acetylcholine receptors according to the invention. For this purpose, a recombinant DNA molecule which comprises at least one nucleic acid according to the invention is introduced into a suitable host cell. The host cell is cultivated in the presence of one or more compounds under conditions which permit expression of the receptors according to the invention. Detection of altered conduction properties makes it possible to find, for example, insecticidal substances.

Alterations in the receptor properties such as, for example, opening of the channel, lack of opening of the channel despite presence of an agonist in sufficient concentration, altered probability or duration of opening lead to corresponding changes in the ion current through the channel. These can be followed directly by, for example, electrophysiological methods (Gopalakrishnan et al. 1995, Buisson et al. 1996, Stetzer et al. 1996, Ragozzino et al. 1997). The ion current can also be followed directly with radiolabelled ions such as, for example, $^{86}$Rb ions (Gopalakrishnan et al. 1996). It is also possible to demonstrate the change in the membrane potential resulting from the ion current using voltage-sensitive dyes. Biological voltage sensors have likewise been described. Changes in the membrane potential additionally lead to a large number of physiological changes in cells, which can be detected directly or indirectly, such as, for example, opening, closing, altered probability or duration of opening of voltage-operated ion channels. These can likewise be detected by the methods described above. If the ion current through the acetylcholine receptor may contain calcium ions, or if the ion current through a secondarily opened channel may contain calcium ions, it is possible to detect the change in concentration of free intracellular calcium for example using calcium-sensitive dyes (Stetzer et al. 1996, Delbono et al. 1997, Staudermann et al. 1998, Zhang et al. 1999). Other known methods for detecting the change in the intracellular calcium concentration are the use of bioluminescent proteins or the use of reporter gene constructs.

The term "agonist" as used herein refers to a molecule which activates acetylcholine receptors.

The term "antagonist" as used herein refers to a molecule whose binding is followed by nonactivation of the receptor, possibly even after binding of an agonist.

The term "modulator" as used herein represents the generic term for agonist and antagonist. Modulators may be small organic chemical molecules, peptides or antibodies which bind to the receptors according to the invention. Modulators may also be small organic chemical molecules, peptides or antibodies which bind to a molecule which in turn binds to the receptors according to the invention and thus influences their biological activity. Modulators may represent mimetics of natural substrates and ligands.

The modulators are preferably small organic chemical compounds.

EXPLANATIONS OF THE SEQUENCE LISTING AND OF THE FIGURES

SEQ ID NO: 1 shows an amino acid sequence region from the α subunit from *Torpedo californica*;
SEQ ID NO: 2 shows the nucleotide sequence of an α subunit according to Example 1A);
SEQ ID NO: 3 shows the amino acid sequence derived from SEQ ID NO: 2;
SEQ ID NO: 4 shows the sequence of primer 1 from Example 1A);

SEQ ID NO: 5 shows the sequence of primer 2 from Example 1A);

SEQ ID NO: 6 shows the nucleotide sequence of an α subunit according to Example 1B);

SEQ ID NO: 7 shows the amino acid sequence derived from SEQ ID NO: 6;

SEQ ID NO: 8 shows the sequence of primer 1 from Example 1B);

SEQ ID NO: 9 shows the sequence of primer 2 from Example 1B);

SEQ ID NO: 10 shows the nucleotide sequence of an α subunit according to Example 1C);

SEQ ID NO: 11 shows the amino acid sequence derived from SEQ ID NO: 10;

SEQ ID NO: 12 shows the sequence of primer 1 from Example 1C);

SEQ ID NO: 13 shows the sequence of primer 2 from Example 1C);

SEQ ID NO: 14 shows the sequence of primer 1 for constructing the vector pBluescript KS$^+$-delta SacI;

SEQ ID NO: 15 shows the sequence of primer 2 for constructing the vector pBluescript KS$^+$-delta SacI;

SEQ ID NO: 16 shows the sequence of primer 3 from Example 1C);

SEQ ID NO: 17 shows the sequence of primer 4 from Example 1C).

FIG. 1A shows a sequence comparison of α subunits of nicotinic acetylcholine receptors from various insect and vertebrate species in the region of the ligand-binding domain.

The sequences were aligned in the region of the putative ligand-binding domain (Changeux et al. 1992) with the aid of the ClustalX program (version 1.81). The region marked by "=" is that homologous to SEQ ID NO:1. "=" identifies the region exchanged in SEQ ID NO: 6. Asterisks identify the region exchanged in SEQ ID NO: 10.

FIG. 1B shows the relationship of the sequences from FIG. 1A as determined with the sequence comparison program njplotwin95 (Perriere et al. 1996) with standard parameters. The program groups the most similar sequences together. It can be seen that all sequences of insect α subunits are more similar to one another than to the sequence of an α subunit expressed in the nervous system of the chick or to the sequence of an α subunit expressed in the muscle of Torpedo or human.

FIG. 2 shows current/time plots derived from acetylcholine receptors expressed in *xenopus* oocytes. The experiments are described in Example 2. Horizontal bars over the plots indicate the periods in which the measurement chamber was perfused with the test solutions indicated above the bars. The L-shaped scale indicates the time axis (horizontal) and current axis (vertical).

A: Receptors containing subunits as shown in SEQ ID NO: 3 and chicken β2

B: Receptors containing chicken α4 and chicken β2 subunits

C: Receptors containing Heliothis virescens α1 and chicken β2 subunits

D: Receptors containing subunits shown in SEQ ID NO: 7 and chicken β2

E: Receptors containing subunits shown in SEQ ID NO: 11 and chicken β2

Figure 3:
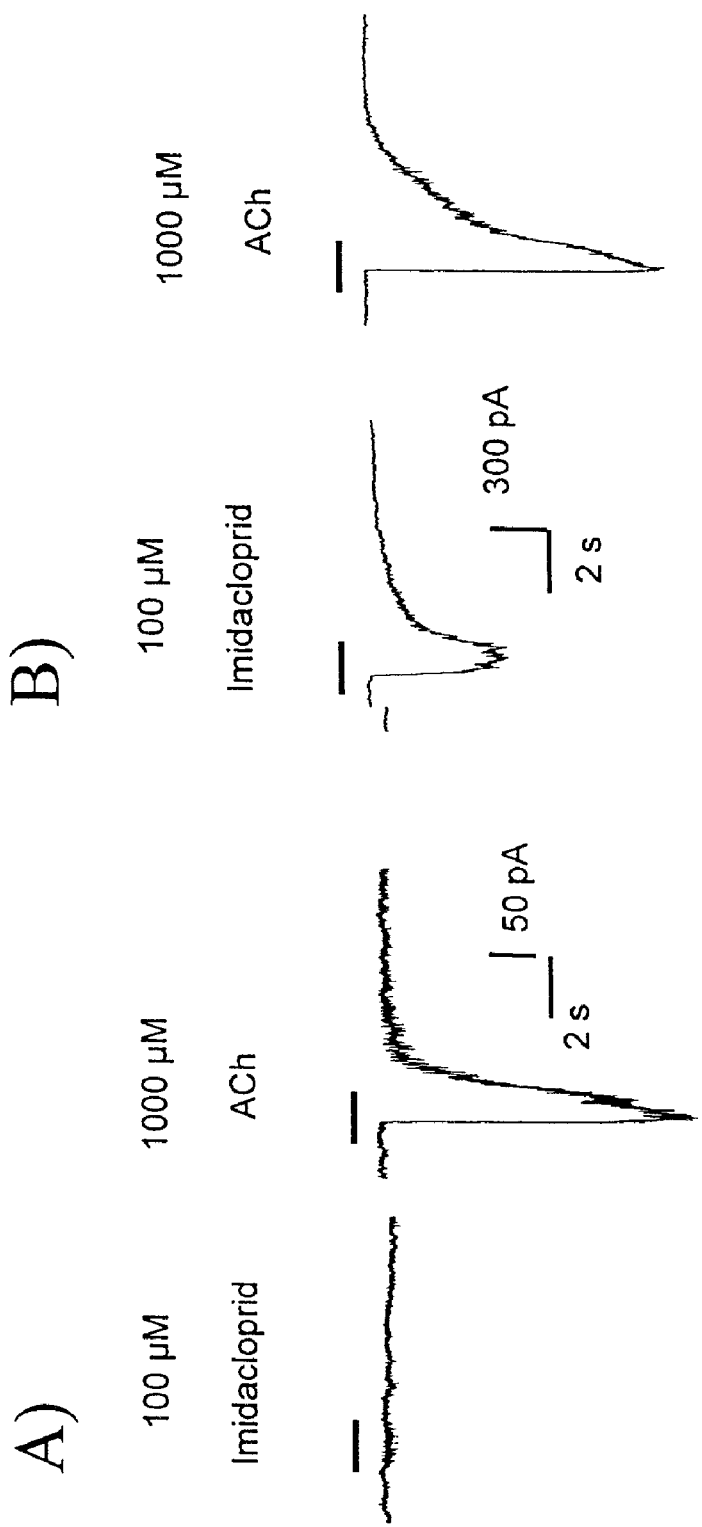

FIG. 3 shows current/time plots derived from acetylcholine receptors expressed in Sf9. The experiments are described in Example 3. Horizontal bars over the plots indicate the periods when the test solutions indicated above the bars were administered. The scale indicates the time axis (horizontal) and current axis (vertical).

A: Receptors containing chicken α4 and chicken β2 units

B: Receptors containing subunits shown in SEQ ID NO: 3 and chicken β2

Figure 4:
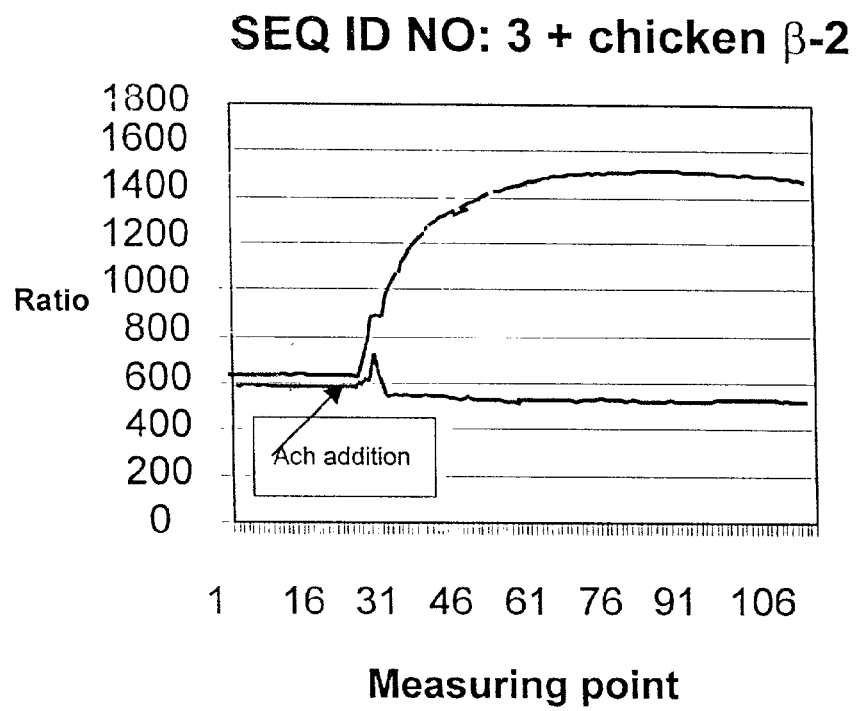
Figure 4:
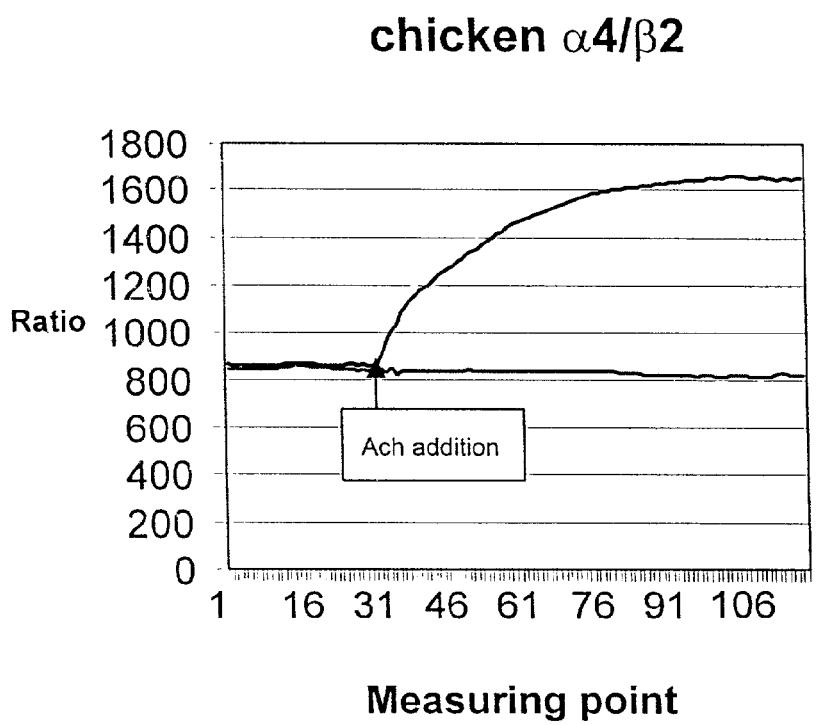

FIG. 4 shows the rise in intracellular calcium in Sf9 cells which expressed the receptors shown in SEQ ID NO: 3 and chicken β2 (top) and chicken α4 and chicken β2 subunits (bottom). The experiments are described in Example 4. The horizontal scale represents the time axis: the distance between two measurement points is 250 ms. The vertical axis represents the relative calcium concentration in the cells on a non-normalized scale. The relative calcium concentration was formed from the ratio of the fluorescence activities of the cells on irradiation with light of wavelengths 340 nm and 380 nm. Row 1 (characterized by ligand-induced rise in the Ca concentration) marks transfected cells, and row 2 nontransfected control cells in the same image field.

EXAMPLES

General

Various nucleic acids coding for modified α subunits were generated.

Besides the nucleic acid shown in SEQ ID NO: 2, further nucleic acids based on the chicken α4 subunit were generated which contain other regions from the ligand-binding amino acid region of the Heliothis virescens α1 subunit (SEQ ID NO: 6, 10). It was not possible with these other modified α subunits to achieve the stated object. No sensitivity for insecticides of the chloronicotinyl type was, for instance, detectable for the α subunits shown in SEQ ID NO: 7, 11. Their pharmacological properties correspond to those of the wild-type chicken α4/β2 receptor and they are thus unsuitable for the abovementioned task.

To obtain, at the same time, the good expression properties of the chicken α4 subunit and the required insect-like pharmacology of the *Heliothis virescens* α1 subunit, a narrowly defined region within the ligand-binding domain of the α subunits is replaced. The polypeptide shown in SEQ ID NO: 3 contains this region.

Example 1

Construction of the Nucleic Acids Described

General

The manipulation of polynucleotides took place by standard methods of recombinant DNA technology (Sambrook et al. 1989). The bioinformatic processing of nucleotide and protein sequences took place with the GCG program package version 10.0 (GCG Genetics Computer Group, Inc., Madison Wis., USA).

A) Construction of the Nucleic Acid Shown in SEQ ID NO: 2 a) The SacI restriction cleavage site in a pBluescript KS$^+$ (Stratagene, Heidelberg, Germany) was deleted using Quickchange (Stratagene, Heidelberg, Germany) in accordance with the manufacturer's instructions and using the following oligonucleotides: SEQ ID NO: 14 (5'-GAACAAAAGCTGGAGGTCCACCGCGGTGGC-3') and SEQ ID NO: 15 (5'-GCCACCGCGGTGGAC-CTCCAGCTTTTGTTC-3').

b) The template used for a polymerase chain reaction (PCR) was the cDNA of the α1 subunit of the Heliothis virescens nicotinic acetylcholine receptor (Genbank AJ000399) in the vector pBluescript KS$^+$ (10 ng/μl). The primers employed were oligonucleotides of the sequence SEQ ID NO: 4 (5'-CACGTGCCCTCCGAGCTCATCTGGCG-GCCGG-3') for the 5' end of the fragment to be amplified and SEQ ID NO: 5 (5'-GTCATATGTCCACGAGC-CGAAC-3') for the 3' end of the fragment in a concentration of 15 pmol/µl in each case. PfuTurbo (Stratagene, Heidelberg, Germany) was used as polymerase. Betaine was employed as 5 M stock solution in water. The nucleotide stock solution contained all 4 nucleotides each in a concentration of 1 mM.

DNA was obtained therefrom by conventional methods. A BamHI/Eco47III fragment was isolated from this DNA.

In parallel to this, the cDNA of the α4 subunit of the chicken nicotinyl acetylcholine receptor was digested with BamHI and Eco47III. The cDNA was cloned into the vector pcDNA3.1$^+$. The BamHI/Eco47III fragment was ligated by conventional methods into the opened cDNA of the chicken α4 subunit. An aliquot of the ligation mixture was transformed into competent *E. coli* cells of the strain DN5α.

| Mixture: | 51.4 µl | of H$_2$O |
| --- | --- | --- |
| | 10 µl | of 10x PfuTurbo buffer (Stratagene, Heidelberg, Germany) |
| | 2 µl | of template DNA (20 ng) |
| | 2 µl | of d'NTP mix, 1 mM each |
| | 2 µl | of primer for the 5' end |
| | 2 µl | of primer for the 3' end |
| | 2.6 µl | of dimethyl sulphoxide (anhydrous) |
| | 26 µl | of betaine |
| | 2 µl | of PfuTurbo polymerase (Stratagene, Heidelberg, Germany) |
| PCR prog.: | (1) 95° C. | 1 min |
| | (2) 95° C. | 30 sec |
| | (3) 55° C. | 30 sec |
| | (4) 72° C. | 30 sec, 29 times back to (2) |
| | (5) 4° C. | Pause |

After the PCR, the reaction product was subcloned using a TOPO-TA kit (Invitrogen, La Jolla, Calif., USA) in accordance with the manufacturer's instructions into a TOPO-TA vector. A colony which contained a plasmid with the amplified fragment was identified by restriction digestion. Plasmid DNA was obtained therefrom by conventional methods. A SacI/NdeI fragment was isolated from this DNA by conventional methods.

In parallel to this, the cDNA of the α4 subunit of the chicken nicotinic acetylcholine receptor (Genbank AJ250361) was cloned into the vector described above in 1Aa (pBluescript KS$^+$ without Sac I) via flanking EcoRI cleavage sites. This plasmid was then digested with SacI and NdeI.

The SacI/NdeI fragment was ligated by conventional methods into the opened cDNA of the chicken α4 subunit. An aliquot of the ligation mixture was transformed by conventional methods into competent *E. coli* cells of the strain DH5α (Gibco, Karlsruhe, Germany).

A colony which contained a plasmid with the fragment ligated in was identified by restriction digestion. Plasmid DNA was obtained therefrom by conventional methods. This plasmid DNA was used for injections into *xenopus* oocytes.

B) Construction of a Nucleic Acid Shown in SEQ ID NO: 6

The so-called insect-typical insertion from the *Heliothis* α1 subunit (coding for RHIDEARGTNVVELG) was inserted into the DNA of the chicken α4 subunit (Genbank AJ250361) in the vector according to 1Aa by Quickchange mutagenesis (Stratagene, Heidelberg, Germany). The mutagenesis was carried out in accordance with the manufacturer's instructions using the following oligonucleotides: SEQ ID NO: 8

(5'-GCTAAGATAGACTTGAGACACATCGATGAGGCTAGAGGAACCAACGT   SEQ ID NO: 9

GGTAGAACTGGGTGTGGACCAACTGGACTACTGG-3')

and (5'-CCAGTAGTCCAGTTGGTCCACACCCAGTTCTACCACGTTGGTTCCTCT

AGCCTCATCGATGTGTCTCAAGTCTATCTTAGC-3').

C) Construction of a Nucleic Acid Shown in SEQ ID NO: 10

The nucleic acid shown in SEQ ID NO: 10 was generated starting from the chicken α4 subunit (Genbank AJ250361) in the vector according to 1Aa by a two-stage Quickchange mutagenesis (Stratagene, Heidelberg, Germany) in accordance with the manufacturer's instructions. The following oligonucleotides were used for the first reaction:

(5'-CAACAGCAAGAAATATGAATGCTGCGACGAGCCCTACCTTGATATAA   SEQ ID NO: 12

CTTTCAACTTCATTATCCGGAGGCTGCCGCTG-3')

-continued and (5'-CAGCGGCAGCCTCCGGATAATGAAGTTGAAAGTTATATCAAGGTAGG      SEQ ID NO: 13

GCTCGTCGCAGCATTCATATTTCTTGCTGTTG-3').

This product was then subjected to a second Quickchange
mutagenesis with the following oligonucleotides:

(5'-GC GGG GAG TGG GTC ATC TTAGAA GTC CCG GCC      SEQ ID NO: 16

GTT CGC AAC GAA AAG TTT TAT ACA TGC TGC GAC GAG CCC TAC C-3')

and (5'-G GTA GGG CTC GTC GCA GCA TGT ATA AAA CTT TTC      SEQ ID NO: 17

GTT GCG AAC GGC CGG GAC TTC AATGAT GAC CCA CTC CCC GC-3').

Example 2

Expression of the Modified Acetylcholine Receptors in *Xenopus* Oocytes

General

In order to characterize the effect of acetylcholine, imidacloprid and other potential agonists of acetylcholine receptors on the modified receptors prepared, electrophysiological measurements were carried out on *xenopus* oocytes. The corresponding methods and experimental designs have been described many times in the literature (see, for example, Kettennann & Grantyn, eds. 1992). Expression of cloned or recombinant receptor genes in *xenopus* oocytes has a number of technical advantages. The oocytes can be stimulated by simple injection of mRNA or cDNA to express the corresponding receptors, and the necessary electrophysiological measurements are possible particularly simply and conveniently on these cells (for example Bertrand et al. 1992, Amar et al. 1993, Cooper et al. 1996).

Expression of the Modified Receptors in *Xenopus* Oocytes

*Xenopus* oocytes were isolated and prepared as previously described (Bertrand et al. 1991). On the first day after isolation of the oocytes, in each case 10 nl of a solution with 2 ng of an appropriate cDNA expression vector were injected into the cell nuclei of the oocytes. The oocytes were kept at 19° C. in a suitable medium (BARTH solution consisting (in mM) of NaCl 88, KCl 1, NaHCO$_3$ 2.4, MgSO$_4$ 0.82, Ca(NO$_3$)$_2$ 0.33, CaCl$_2$ 0.41, HEPES 10, pH 7.4) for 3–5 days. After this time, the electrophysiological experiments were carried out.

Electrophysiological Experiments

Electrophysiological recordings were carried out using a dual electrode voltage clamp by tried and tested methods which are well known (compare Bertrand et al. 1992). Each oocyte was placed singly in a measurement chamber and pierced by two microelectrodes. The microelectrodes are fine glass capillaries filled with a suitable salt solution (for example 3 M KCl or 1.5 M K acetate with 100 mM KCl) and then have a series resistance of 0.3–1.2 M Ohm. The membrane voltage was fixed at −80 mV using a voltage clamp amplifier (TEC-00, npi, Tamm, Germany), and the inward current flowing through the cell membrane was measured and recorded by computer. Frog Ringer solution containing 115 mM NaCl; 2.5 mM KCl; 1.8 mM CaCl$_2$; 10 mM HEPES; at pH 7.4 (adjusted with NaOH) flowed at a flow rate of 5–10 ml/minute through the measurement chamber. In order to test acetylcholine, imidacloprid or another active substance on these oocytes, the substance was added in the intended concentration to the frog Ringer solution and the perfusion of the measurement chamber was briefly changed over to this test solution. Acetylcholine (Fluka, Buchs, Switzerland) was stored as stock solution at −20° C. and added to the measurement solution immediately before the experiment.

All modified receptors responding to acetylcholine were then also tested with imidacloprid. In this case it is immediately evident from the occurrence of an additional inward current signal whether the receptor variant expressed in the particular oocyte can be activated by imidacloprid or not.

In order to characterize the sensitivity of the modified receptors to acetylcholine and imidacloprid in more detail, dose-effect plots were recorded by repeating the experiment described above with different concentrations of the substance. The display of the relative signal strengths (based on the current response induced by a standard dose of acetylcholine, in this case usually 0.32 μM) against the concentration of the test substance permits a direct comparison of which receptor variants are particularly sensitive to imidacloprid since considerably lower concentrations of imidacloprid are necessary to induce a current signal.

Results are detailed in FIG. 2. Receptors comprising unmodified chicken α4 subunits and chicken β2 subunits respond to addition of acetylcholine, but not imidacloprid, with ligand-induced conductance (FIG. 2B), whereas receptors comprising unmodified *Heliothis* α1 subunits and chicken β2 subunits are sensitive to both acetylcholine and imidacloprid (FIG. 2C). Receptors consisting of the chicken β2 subunit and polypeptides according to SEQ ID NOs: 3, 7 and 11, respectively, are all functional, i.e. they display ligand-induced conductance upon addition of acetylcholine (FIGS. 2A, E, F). This is in itself surprising, given the results of van den Beukel (van den Beukel 1998). However, only the receptors consisting of the chicken β2 subunit and polypeptides according to SEQ ID NO: 3 are sensitive to imidacloprid (FIG. 2A).

Example 3

Functional Expression of a Modified Acetylcholine Receptor in Sf9 Cell Lines Containing the Modified Subunit Shown in SEQ ID NO: 3

*Spodoptera frugiperda* 9 (Sf9) cells were transfected simultaneously with cDNA expression plasmids which code for the modified heliothis/chicken subunit and for the chicken β2 subunit using a liposomal transfection reagent (DAC-30, Eurogentec, Belgium). A cDNA expression construct for the green fluorescent protein from *Aequoria victoria* was transfected simultaneously. This makes it possible simply to identify transfected cells because experience has shown that most of the cells which have taken up one of the constructs have also taken up the other ones. 24 to 48 hours after transfection, the currents through the cell membrane of the Sf9 cells were measured by whole-cell recordings. For this purpose, the potential difference across the cell membrane was kept constant at −70 mV. Substances were applied using the U-tube reversed flow technique (Fenwick 1982). The volume of the experimental chamber, which was continuously perfused with bath solution (3 ml/min), was less than 0.5 ml. The standard perfusion solution (extracellular medium) had the following composition (in mM): 150 NaCl, 4 KCl, 2 $MgCl_2$, 2 $CaCl_2$, 10 HEPES (pH 7.3). The pipette solution contained (in mM): 150 KCl, 10 HEPES 10 K-EGTA (pH 7.2). The microelectrodes were produced in an electrode puller (Zeitz, Germany) from borosilicate glass blanks (external diameter 1.6 mm, Hilgenberg, Germany). The resistance of the flame-polished microelectrodes on use of the abovementioned pipette and bath solutions was between 4 and 6 MΩ. All the experiments were carried out at room temperature (22–25° C.) with an L/M EPC7 patch clamp amplifier (List electronic). The analogue signals were filtered using 8-pole Bessel filters to 315 Hz and digitized with 1 kHz. The software used to record and analyse the data was pClamp (version 6.06). After the "giga seal" was reached, the fast interfering capacitances (pipette capacitance) were compensated with the C-fast compensation mode of the EPC-7. No compensation of the series resistance (cell capacitance) was carried out.

To check whether expression of the cDNAs which code for the modified heliothis/chicken subunit shown in SEQ ID NO: 3 and the chicken β2 subunit led to the production of functional acetylcholine receptors in the cells, whole-cell recordings were carried out by the method described above, during which the cells were stimulated with acetylcholine (1000 μM) or imidacloprid (100 μM). Immediately after the stimulus it was possible to measure strong inward currents typical of the activation of ion channels, both on application of 1000 μM acetylcholine and on application of 100 μM imidacloprid (FIG. 3). In order to quantify the results, a series of experiments was carried out with 5 measurements. This involved comparison of the inward currents induced by 100 μM imidacloprid with the inward currents induced by 1000 μM acetylcholine. The amplitude ratio (maximum amplitude of the current/time plot on application of 100 μM imidacloprid divided by the maximum amplitude of the current/time plot on application of 1000 μM acetylcholine) is a relative measure of the sensitivity of a receptor for imidacloprid. This amplitude ratio for the receptor containing polypeptide shown in SEQ ID NO: 3 and the chicken β2 subunit was 0.46±0.09 (n=5 cells). By contrast, there were either no or only very weak inward currents on Sf9 cells transfected simultaneously with cDNA expression plasmids coding for the chicken α4 subunit and the chicken β2 subunit on application of 100 μM imidacloprid. The amplitude ratio for these receptors was 0.05±0.06 (n=5 cells). Untransfected control cells in the same experiment, which were identifiable through the absence of the fluorescence of the green fluorescent protein, showed no response either to acetylcholine or to imidacloprid.

These results show that the acetylcholine receptor subunit with an amino acid sequence shown in SEQ ID NO: 3 forms together with the chicken β2 subunit a functional receptor in Sf9 cells which is clearly distinguished pharmacologically from recombinantly expressed chicken α4-β2 receptor.

Example 4

Detection by Calcium Imaging of the Activation by Agonists of the Acetylcholine Receptors Expressed in Cells and Containing a Subunit Shown in SEQ ID NO: 3

Cell Culture and Gene Transfer

Sf9 cells were cultivated in a mixture of ¾ TC100 medium (Gibco, Karlsruhe, Germany)+¼ SF900 medium (Gibco, Karlsruhe, Germany), 10% fetal calf serum, 0.1% Pluronic (Gibco, Karlsruhe, Germany) at 27° C. DAC-30 (Eurogentec) was used for the gene transfer in accordance with the manufacturer's instructions. An expression construct for the green fluorescent protein from *Aequoria victoria* was transfected simultaneously as further CDNA. This permitted simple identification of transfected cells because experience has shown that most of the cells which have taken up one of the constructs have also taken up the other ones. 24 to 48 hours after the gene transfer, the cells were seeded in various densities in microtitre plates.

Fura-2 Measurements

The changes in the intracellular calcium concentration were measured using Fura-2. A stock solution containing 2 mM Fura-2 acetoxymethyl ester (Sigma, Munich, Germany) in dimethyl sulphoxide (DMSO) was diluted to a final concentration of 10 μM in ¾ TC100 medium (Gibco, Karlsruhe, Germany)+¼ SF900 medium (Gibco, Karlsruhe, Germany) with 2% bovine serum albumin (Sigma, Munich, Germany). The cells were incubated in a microtitre plate in this solution for 45 to 60 minutes. The cells were then washed twice in N-(2-hydroxyethyl)piperazine-N'-(2-ethanesulphonic acid) (5 mM HEPES)-buffered calcium buffer (HEPES-buffered salt solution, pH 7.2 with 84 mM $CaCl_2$). 100 μl of Tyrode buffer were placed in the wells of the microtitre plate, and the cells were irradiated under a fluorescence microscope (Axiovert, Zeiss, Jena, Germany) with light of wavelengths 340 nm and 380 nm alternately. A series of video images (120 images) with a time resolution of 250 msec was recorded using a TILL Imago CCD/Polychrom image analysis system (T.I.L.L. Photonics, Martinsried, Germany). After 30 images had been recorded, the cells were stimulated by adding 600 μl of 2 mM acetylcholine chloride in calcium buffer (final concentration of acetylcholine=1 mM, arrow in FIG. 4). The data were then analysed using the TILL Vision software (3.3, T.I.L.L. Photonics, Martinsried, Germany): the cells in an image field were separated into a transfected and a nontransfected population on the basis of expression of the green fluorescent protein. For each population separately the fluorescence intensity of the cells on irradiation with light of wavelength 380 nm was divided by the corresponding intensity at 340 nm, thus forming a ratio which represents the relative rise in calcium concentration on a non-normalized scale (similar to Grynkiewicz et al. 1985).

The results (FIG. 4) show that acetylcholine receptors containing a subunit shown in SEQ ID NO: 3 can be functionally expressed in cell culture cells, and stimulation thereof leads to a rise in the calcium concentration in the cell.

REFERENCES

Amar et al. 1995, A nicotinic acetylcholine receptor subunit from insect brain forms a non-desensitizing homo-oligomeric nicotinic acetylcholine receptor when expressed in Xenopus oocytes, Neuroscience Letters 199, 107–110.

Amar et al. 1993, Agonist pharmacology of the neuronal a7 nicotinic receptor expressed in Xenopus oocytes, FEBS Lett. 327, 284–288.

Bertrand et al. 1994, Physiological properties of neuronal nicotinic receptors reconstituted from the vertebrate beta 2 subunit and Drosophila alpha subunits, Eur. J. Neurosci. 6, 869–75.

Bertrand et al. 1992, Pharmacological properties of the homomeric alpha-7 receptor, Neurosci. Lett. 146, 87–90.

Bertrand et al. 1991, Methods in Neuroscience 4, New York, Academic Press, 174–193.

Breer et al. 1987, Molecular properties and functions of insect acetylcholine receptors, J. Insect Physiol. 33, 771–790.

Buckingham et al. 1997, Imidacloprid actions on insect neuronal acetylcholine receptors, J. Exp. Biol. 200, 2685–2692.

Buisson et al. 1996, Human $\alpha 3/\beta 4$ Neuronal Nicotinic Acetylcholine Receptor in HEK-293 cells: A Patch-Clamp Study, J Neuroscience 16, 7880–7891.

Changeux et al. 1992, The functional architecture of the nicotinic acetylcholine receptor explored by affinity labelling and site-directed mutagenesis, Quarterly Review of Biophysics 25, 395–432.

Claudio et al. 1983, Nucleotide and deduced amino acid sequences of Torpedo califomica acetylcholine receptor y subunit, Proc. Natl. Acad. Sci. USA 80, 1111–1115.

Cooper et al. 1996, Pharmacology of the nicotinic acetylcholine receptor from fetal rat muscle expressed in Xenopus oocytes, Eur. J. Pharmacol. 309, 287–298.

Delbono et al. 1997, Activation of the Recombinant Human $\alpha 7$ Nicotinic Acetylcholine Receptor Significantly Raises Intracellular Free Calcium; J. Pharmacol. Exp. Therapeut. 280, 428–438.

Devillers-Thiery et al. 1983, Complete mRNA coding sequence of the acetylcholine binding $\alpha$-subunit of Torpedo marmorata acetylcholine receptor: a model for the transmembrane organization of the polypeptide chain, Proc. Natl. Acad. Sci. USA 80, 2067–2071.

Eastham et al. 1998, Characterisation of a nicotinic acetylcholine receptor from the insect Manduca sexta, Eur. J. Neurosci 10, 879–889.

Elgoyhen et al. 1997, U.S. Pat. No. 5,683,912.

Gopalakrishnan et al. 1995, Stable Expression and Pharmacological Properties of the Human $\alpha 7$ nicotinic acetylcholine receptor, Eur. J. Pharmacol. 290, 237–246.

Gopalakrishnan et al. 1996, Stable Expression and Pharmacological Properties of the Human Neuronal Nicotinic Acetylcholine $\alpha 4/\beta 2$ receptor, J. Pharmacol. Exp. Therapeut. 276, 289–297.

Grynkiewicz et al. 1985, A new generation of Ca2+ indicators with greatly improved fluorescence properties, J. Biol. Chem. 260, 3440–3450.

Heinemann et al. 1997, U.S. Pat. No 5,591,590.

Hermans-Borgmeyer et al. 1986, Primary structure of a developmentally regulated nicotinic acetylcholine receptor protein from Drosophila, EMBO J. 5, 1503–1508.

Hermsen et al. 1998, Neuronal nicotinic receptors in the locust Locusta migratoria. Cloning and expression, J. Biol. Chem. 17, 18394–404.

Huang et al. 1999, Molecular characterization and imidacloprid selectivity of nicotinic acetylcholine receptor subunits from the peach-potato aphid myzus persicae J. Neurochem. 73, 380–389.

Jespersen et al. 1997, Efficient Non-PCR-Mediated Overlap Extension of PCR Fragments by Exonuclease "End Polishing", Biotechniques, 23, 48.

Lansdell et al. 1997, Temperature-sensitive expression of Drosophila neuronal nicotinic acetylcholine receptors, J. Neurochem. 68, 1812–9.

Lansdell et al. 2000, The influence of nicotinic receptor subunit composition upon agonist, alpha-bungarotoxin and insecticide (imidacloprid) binding affinity, Neuropharmacology 39, 671–9.

Lindstrom et al. 1997, U.S. Pat. No. 5,599,709.

Marshall et al. 1990, Sequence and functional expression of a single $\alpha$ subunit of an insect nicotinic acetylcholine receptor, EMBO J. 9, 4391–4398.

Matsuda et al. 1998, Effects of the subunit on imidacloprid sensitivity of recombinant nicotinic acetylcholine receptors, Br. J. Pharmacol. 123, 518–524.

Noda et al. 1982, Primary structure of $\alpha$-subunit precursor of Torpedo califomica acetylcholine receptor deduced from cDNA sequence, Nature 299, 793–797.

Noda et al. 1983a, Primary structures of $\beta$- and $\delta$-subunit precursor of Torpedo californica acetylcholine receptor deduced from cDNA sequences, Nature 301, 251–255.

Noda et al. 1983b, Structural homology of Torpedo californica acetylcholine receptor subunits, Nature 302, 528–532.

Ortells et al. 1995, Evolutionary history of the ligand-gated ion-channel superfamily of receptors, Trends in Neuroscience 18, 121–127.

Perriere et al. 1996, WWW-Query: An on-line retrieval system for biological sequence banks. Biochimie 78, 364–369

Ragozzino et al. 1997, Functional Properties of Neuronal Nicotinic Acetylcholine Receptor Channels Expressed in Transfected Human Cells, Eur. J. Neurosci. 9, 480–488.

Sawruk et al. 1990a, Heterogeneity of Drosophila nicotinic acetylcholine receptors: SAD, a novel developmentally regulated $\alpha$-subunit. EMBO J. 9, 2671–2677.

Sawruk et al. 1990b, SBD, a novel structural subunit of the Drosophila nicotinic acetylcholine receptor, shares its genomic localization with two $\alpha$-subunits, FEBS Lett. 273, 177–181.

Schloβ et al. 1988, Neuronal acetylcholine receptors of Drosophila: the ARD protein is a component of a high-affinity $\alpha$-bungarotoxin binding complex, EMBO J 7, 2889–2984.

Schoepfer et al. 1990, Brain alpha-bungarotoxin binding protein cDNAs and MAbs reveal subtypes of this branch of the ligand-gated ion channel gene superfamily; Neuron 5, 35–48.

Schulz et al. 1998, D 3, a new functional -subunit of nicotinic acetylcholine receptors from Drosophila, J. Neurochem. 71, 853–862.

Schulz et al. 2000, Neuronal nicotinic acetylcholine receptors from Drosophila: two different types of alpha subunits coassemble within the same receptor complex, J. Neurochem. 74, 2537–46.

Sgard et al. 1998, Cloning and Functional Characterization of Two Novel Nicotinic Acetylcholine Receptor $\alpha$ subunits form the Insect Pest *Myzus persicae*; J. Neurochem 71, 903–912.

Staudermann et al. 1998, Characterization of Human Recombinant Nicotinic Acetylcholine Receptor Subunit α2β4, α3β4 and α4β4 Combinations Stably Expressed in HEK-293 Cells, J. Pharmacol. Exp. Therapeut. 284, 777–789.

Stetzer et al. 1996, Stable expression in HEK-293 cells of the rat α3/β4 subtype of neuronal nicotinic acetylcholine receptor, FEBS Lett. 397, 39–44.

Thompson et al. 1997, The ClustalX windows interface: flexible strategies for multiple sequence alignment aided by quality analysis tools, Nucleic Acids Research 24, 4876–4882.

Van den Beukel 1998, Species- and subtype-specific interactions of cholinesterase inhibitors with acetylcholine receptors, Dissertation Utrecht University, ISBN 90-393-1737-2.

Zhang et al. 1999, Activation and Ca2+ Permeation of Stably Transfected α3/β4 Neuronal Nicotinic Acetylcholine receptor; Mol. Pharnacol. 55, 970–981.

What is claimed is:

1. A modified acetylcholine receptor subunit comprising the amino acid sequence shown in SEQ ID NO: 3, wherein the modified acetylcholine receptor subunit comprises an α subunit of a vertebrate acetylcholine receptor having a region which is homologous with the amino acid sequence shown in SEQ ID NO: 1, wherein at least one amino acid in the region of the α subunit of the vertebrate acetylcholine receptor which is homologous with the amino acid sequence shown in SEQ ID NO: 1 is replaced by an amino acid which occurs at the identical position in the corresponding region of an α subunit of an insect acetylcholine receptor, and wherein the replacement of the at least one amino acid in the region of the α subunit results in a change of the amino acid sequence when compared with the amino acid sequence of the α subunit wherein no replacement has occurred.

2. A nucleic acid comprising a nucleotide sequence which codes for a modified acetylcholine receptor subunit, wherein the modified acetylcholine receptor subunit comprises an α subunit of a vertebrate acetylcholine receptor having a region which is homologous with the amino acid sequence shown in SEQ ID NO: 1, wherein at least one amino acid in the region of the α subunit of the vertebrate acetylcholine receptor which is homologous with the amino acid sequence shown in SEQ ID NO: 1 is replaced by an amino acid which occurs at the identical position in the corresponding region of an α subunit of an insect acetylcholine receptor, and wherein the replacement of the at least one amino acid in the region of the α subunit results in a change of the amino acid sequence when compared with the amino acid sequence of the α subunit wherein no replacement has occurred, and wherein the nucleotide sequence comprises the sequence shown in SEQ ID NO: 2.

3. A modified acetylcholine receptor comprising an acetylcholine receptor subunit of claim 1.

4. A DNA construct comprising SEQ ID NO: 2 and a heterologous promoter.

5. A vector comprising a DNA construct according to claim 4.

6. A vector according to claim 5, wherein the nucleic acid is functionally linked to regulatory sequences which ensure expression of the nucleic acid in prokaryotic or eukaryotic cells.

7. A host cell containing a DNA construct according to claim 4.

8. An isolated acetylcholine receptor comprising β subunit and an α subunit, wherein the α subunit comprises SEQ ID NO: 3.

* * * * *

SEQUENCE LISTING

<160> NUMBER OF SEQ ID NOS: 17

<210> SEQ ID NO 1
<211> LENGTH: 45
<212> TYPE: PRT
<213> ORGANISM: Torpedo californica

<400> SEQUENCE: 1

```
Asp Phe Ala Ile Val His Met Thr Lys Leu Leu Leu Asp Tyr Thr Gly
 1               5                  10                  15

Lys Ile Met Trp Thr Pro Pro Ala Ile Phe Lys Ser Tyr Cys Glu Ile
             20                  25                  30

Ile Val Thr His Phe Pro Phe Asp Gln Gln Asn Cys Thr
         35                  40                  45
```

<210> SEQ ID NO 2
<211> LENGTH: 1869
<212> TYPE: DNA
<213> ORGANISM: Artificial Sequence
<220> FEATURE:
<221> NAME/KEY: CDS
<222> LOCATION: (1)..(1866)
<223> OTHER INFORMATION: Description of Artificial Sequence: Modified alpha 4 subunit of the chicken nicotinic acetylcholine receptor

<400> SEQUENCE: 2

```
atg gga ttt ctc gtg tcg aag gga aac ctc ctc ctg ctg tgt gcc        48
Met Gly Phe Leu Val Ser Lys Gly Asn Leu Leu Leu Leu Cys Ala
 1               5                  10                  15 agc atc ttc ccc gct ttc ggc cac gtg gaa acg cga gcc cat gcg gag   96
Ser Ile Phe Pro Ala Phe Gly His Val Glu Thr Arg Ala His Ala Glu
             20                  25                  30 gag cgc ctc ctg aag aaa ctc ttc tcc ggg tat aac aag tgg tcc cgt  144
Glu Arg Leu Leu Lys Lys Leu Phe Ser Gly Tyr Asn Lys Trp Ser Arg
         35                  40                  45 ccc gtc gcc aac att tcg gat gtg gtc ctg gtc cgc ttc ggc ttg tcc  192
Pro Val Ala Asn Ile Ser Asp Val Val Leu Val Arg Phe Gly Leu Ser
     50                  55                  60 ata gcc cag ctc atc gat gtt gat gag aag aac caa atg atg acc aca  240
Ile Ala Gln Leu Ile Asp Val Asp Glu Lys Asn Gln Met Met Thr Thr
 65                  70                  75                  80 aat gtg tgg gtg aag cag gag tgg cac gac tac aag ctg cgc tgg gac  288
Asn Val Trp Val Lys Gln Glu Trp His Asp Tyr Lys Leu Arg Trp Asp
                 85                  90                  95 ccc cag gag tat gaa aac gtc aca tcc atc cga atc ccc tca gag ctc  336
Pro Gln Glu Tyr Glu Asn Val Thr Ser Ile Arg Ile Pro Ser Glu Leu
            100                 105                 110
```

-continued

| | |
|---|---|
| atc tgg cgg ccg gac ata gtc ctc tac aac aat gcc gac ggc aac ttc<br>Ile Trp Arg Pro Asp Ile Val Leu Tyr Asn Asn Ala Asp Gly Asn Phe<br>     115                 120                 125 | 384 |
| gag gta acg ctg gcg acg aag gcg act ttg aat tat acg gga cgt gtg<br>Glu Val Thr Leu Ala Thr Lys Ala Thr Leu Asn Tyr Thr Gly Arg Val<br>130                 135                 140 | 432 |
| gag tgg cgc ccg ccg gct atc tac aag tcc tcg tgc gag atc gac gtg<br>Glu Trp Arg Pro Pro Ala Ile Tyr Lys Ser Ser Cys Glu Ile Asp Val<br>145                 150                 155                 160 | 480 |
| gaa tac ttc ccg ttc gac cag cag acg tgc gtc atg aag ttc ggc tcg<br>Glu Tyr Phe Pro Phe Asp Gln Gln Thr Cys Val Met Lys Phe Gly Ser<br>                 165                 170                 175 | 528 |
| tgg aca tat gac aaa gct aag ata gac ttg gtg agc atg cat agc cat<br>Trp Thr Tyr Asp Lys Ala Lys Ile Asp Leu Val Ser Met His Ser His<br>             180                 185                 190 | 576 |
| gtg gac caa ctg gac tac tgg gaa agc ggg gag tgg gtc atc att aat<br>Val Asp Gln Leu Asp Tyr Trp Glu Ser Gly Glu Trp Val Ile Ile Asn<br>         195                 200                 205 | 624 |
| gcc gtg ggc aat tac aac agc aag aaa tat gaa tgc tgc aca gag atc<br>Ala Val Gly Asn Tyr Asn Ser Lys Lys Tyr Glu Cys Cys Thr Glu Ile<br>     210                 215                 220 | 672 |
| tac cct gat ata act tac tcc ttc att atc cgg agg ctg ccg ctg ttc<br>Tyr Pro Asp Ile Thr Tyr Ser Phe Ile Ile Arg Arg Leu Pro Leu Phe<br>225                 230                 235                 240 | 720 |
| tac aca atc aat ttg atc att ccc tgc ctg ctt atc tcc tgc ttg act<br>Tyr Thr Ile Asn Leu Ile Ile Pro Cys Leu Leu Ile Ser Cys Leu Thr<br>                 245                 250                 255 | 768 |
| gtc ctg gtc ttc tac cta ccc tct gag tgc gga gag aag ata acc ttg<br>Val Leu Val Phe Tyr Leu Pro Ser Glu Cys Gly Glu Lys Ile Thr Leu<br>             260                 265                 270 | 816 |
| tgc atc tct gtg ctg cta tcc ctc acg gtg ttc ctg ctc atc aca<br>Cys Ile Ser Val Leu Leu Ser Leu Thr Val Phe Leu Leu Leu Ile Thr<br>         275                 280                 285 | 864 |
| gag atc atc cct tct acc tcc ctg gtc atc ccc ctg ata gga gag tat<br>Glu Ile Ile Pro Ser Thr Ser Leu Val Ile Pro Leu Ile Gly Glu Tyr<br>     290                 295                 300 | 912 |
| ctg ctc ttc acc atg ata ttt gtc acc ttg tct atc atc atc act gtc<br>Leu Leu Phe Thr Met Ile Phe Val Thr Leu Ser Ile Ile Ile Thr Val<br>305                 310                 315                 320 | 960 |
| ttt gtg ctc aac gta cac cac cgt tca cca cgt acc cac acg atg cct<br>Phe Val Leu Asn Val His His Arg Ser Pro Arg Thr His Thr Met Pro<br>                 325                 330                 335 | 1008 |
| gac tgg gtg agg agg gtc ttc ctt gac ata gtc cca cgt ctc ctc ttc<br>Asp Trp Val Arg Arg Val Phe Leu Asp Ile Val Pro Arg Leu Leu Phe<br>             340                 345                 350 | 1056 |
| atg aag cgg ccc tcc aca gtg aaa gac aat tgc aag aag ctt att gaa<br>Met Lys Arg Pro Ser Thr Val Lys Asp Asn Cys Lys Lys Leu Ile Glu<br>         355                 360                 365 | 1104 |
| tct atg cac aaa cta acc aac tca cca agg ctt tgg tct gag acc gac<br>Ser Met His Lys Leu Thr Asn Ser Pro Arg Leu Trp Ser Glu Thr Asp<br>     370                 375                 380 | 1152 |
| atg gag ccc aac ttc act acc tca tcc tcc ccc agc ccc cag agt aat<br>Met Glu Pro Asn Phe Thr Thr Ser Ser Ser Pro Ser Pro Gln Ser Asn<br>385                 390                 395                 400 | 1200 |
| gaa cct tca ccc aca tct tcc ttc tgt gcc cac ctt gag gag cca gcc<br>Glu Pro Ser Pro Thr Ser Ser Phe Cys Ala His Leu Glu Glu Pro Ala<br>                 405                 410                 415 | 1248 |
| aaa cct atg tgc aaa tcc cct tct gga cag tac tca atg ctg cac cct<br>Lys Pro Met Cys Lys Ser Pro Ser Gly Gln Tyr Ser Met Leu His Pro | 1296 |

-continued

```
              420                 425                 430
gag ccc cca cag gtg acg tgt tcc tct ccg aag ccc tcc tgc cac ccc    1344
Glu Pro Pro Gln Val Thr Cys Ser Ser Pro Lys Pro Ser Cys His Pro
            435                 440                 445 ctg agt gac acc cag acc aca tct atc tca aaa ggc aga tcg ctc agt    1392
Leu Ser Asp Thr Gln Thr Thr Ser Ile Ser Lys Gly Arg Ser Leu Ser
        450                 455                 460 gtt cag cag atg tac agc ccc aat aag aca gag gaa ggg agc atc cgc    1440
Val Gln Gln Met Tyr Ser Pro Asn Lys Thr Glu Glu Gly Ser Ile Arg
465                 470                 475                 480 tgt agg tcc cga agc atc cag tac tgt tac ctg cag gag gac tct tcc    1488
Cys Arg Ser Arg Ser Ile Gln Tyr Cys Tyr Leu Gln Glu Asp Ser Ser
                485                 490                 495 cag acc aat ggc cac tct agt gcc tct cca gcg tcg cag cgc tgc cac    1536
Gln Thr Asn Gly His Ser Ser Ala Ser Pro Ala Ser Gln Arg Cys His
            500                 505                 510 ctc aat gaa gag cag ccc cag cac aag ccc cac cag tgc aag tgt aag    1584
Leu Asn Glu Glu Gln Pro Gln His Lys Pro His Gln Cys Lys Cys Lys
        515                 520                 525 tgc aga aag gga gag gca gct ggc aca ccg act caa gga agc aag agc    1632
Cys Arg Lys Gly Glu Ala Ala Gly Thr Pro Thr Gln Gly Ser Lys Ser
530                 535                 540 cac agc aac aaa gga gaa cac ctc gtg ctg atg tcc cca gcc ctg aag    1680
His Ser Asn Lys Gly Glu His Leu Val Leu Met Ser Pro Ala Leu Lys
545                 550                 555                 560 ctg gcg gtg gaa ggg gtc cac tac att gca gac cac ctg cga gca gaa    1728
Leu Ala Val Glu Gly Val His Tyr Ile Ala Asp His Leu Arg Ala Glu
                565                 570                 575 gat gca gat ttc tca gtg aag gaa gac tgg aag tac gta gca atg gtc    1776
Asp Ala Asp Phe Ser Val Lys Glu Asp Trp Lys Tyr Val Ala Met Val
            580                 585                 590 att gac cgg atc ttt ctc tgg atg ttc atc atc gtg tgt ttg ctg ggg    1824
Ile Asp Arg Ile Phe Leu Trp Met Phe Ile Ile Val Cys Leu Leu Gly
        595                 600                 605 acc gtt ggg ctc ttc ctc ccg ccg tgg ctg gca gga atg atc taa        1869
Thr Val Gly Leu Phe Leu Pro Pro Trp Leu Ala Gly Met Ile
610                 615                 620
```

<210> SEQ ID NO 3
<211> LENGTH: 622
<212> TYPE: PRT
<213> ORGANISM: Artificial Sequence
<220> FEATURE:
<223> OTHER INFORMATION: Description of Artificial Sequence: Modified
      alpha 4 subunit of the chicken nicotinic acetylcholine
      receptor

<400> SEQUENCE: 3

```
Met Gly Phe Leu Val Ser Lys Gly Asn Leu Leu Leu Leu Cys Ala
  1               5                  10                  15

Ser Ile Phe Pro Ala Phe Gly His Val Glu Thr Arg Ala His Ala Glu
                 20                  25                  30

Glu Arg Leu Leu Lys Lys Leu Phe Ser Gly Tyr Asn Lys Trp Ser Arg
            35                  40                  45

Pro Val Ala Asn Ile Ser Asp Val Val Leu Val Arg Phe Gly Leu Ser
        50                  55                  60

Ile Ala Gln Leu Ile Asp Val Asp Glu Lys Asn Gln Met Met Thr Thr
 65                  70                  75                  80

Asn Val Trp Val Lys Gln Glu Trp His Asp Tyr Lys Leu Arg Trp Asp
                 85                  90                  95
```

```
Pro Gln Glu Tyr Glu Asn Val Thr Ser Ile Arg Ile Pro Ser Glu Leu
            100                 105                 110

Ile Trp Arg Pro Asp Ile Val Leu Tyr Asn Asn Ala Asp Gly Asn Phe
            115                 120                 125

Glu Val Thr Leu Ala Thr Lys Ala Thr Leu Asn Tyr Thr Gly Arg Val
            130                 135                 140

Glu Trp Arg Pro Ala Ile Tyr Lys Ser Ser Cys Glu Ile Asp Val
145                 150                 155                 160

Glu Tyr Phe Pro Phe Asp Gln Gln Thr Cys Val Met Lys Phe Gly Ser
                    165                 170                 175

Trp Thr Tyr Asp Lys Ala Lys Ile Asp Leu Val Ser Met His Ser His
                180                 185                 190

Val Asp Gln Leu Asp Tyr Trp Glu Ser Gly Glu Trp Val Ile Ile Asn
            195                 200                 205

Ala Val Gly Asn Tyr Asn Ser Lys Lys Tyr Glu Cys Cys Thr Glu Ile
            210                 215                 220

Tyr Pro Asp Ile Thr Tyr Ser Phe Ile Ile Arg Arg Leu Pro Leu Phe
225                 230                 235                 240

Tyr Thr Ile Asn Leu Ile Ile Pro Cys Leu Leu Ile Ser Cys Leu Thr
                245                 250                 255

Val Leu Val Phe Tyr Leu Pro Ser Glu Cys Gly Glu Lys Ile Thr Leu
                260                 265                 270

Cys Ile Ser Val Leu Leu Ser Leu Thr Val Phe Leu Leu Leu Ile Thr
                275                 280                 285

Glu Ile Ile Pro Ser Thr Ser Leu Val Ile Pro Leu Ile Gly Glu Tyr
            290                 295                 300

Leu Leu Phe Thr Met Ile Phe Val Thr Leu Ser Ile Ile Ile Thr Val
305                 310                 315                 320

Phe Val Leu Asn Val His His Arg Ser Pro Arg Thr His Thr Met Pro
                325                 330                 335

Asp Trp Val Arg Arg Val Phe Leu Asp Ile Val Pro Arg Leu Leu Phe
                340                 345                 350

Met Lys Arg Pro Ser Thr Val Lys Asp Asn Cys Lys Lys Leu Ile Glu
            355                 360                 365

Ser Met His Lys Leu Thr Asn Ser Pro Arg Leu Trp Ser Glu Thr Asp
            370                 375                 380

Met Glu Pro Asn Phe Thr Thr Ser Ser Pro Ser Pro Gln Ser Asn
385                 390                 395                 400

Glu Pro Ser Pro Thr Ser Ser Phe Cys Ala His Leu Glu Pro Ala
                    405                 410                 415

Lys Pro Met Cys Lys Ser Pro Ser Gly Gln Tyr Ser Met Leu His Pro
                420                 425                 430

Glu Pro Pro Gln Val Thr Cys Ser Ser Pro Lys Pro Ser Cys His Pro
                435                 440                 445

Leu Ser Asp Thr Gln Thr Thr Ser Ile Ser Lys Gly Arg Ser Leu Ser
    450                 455                 460

Val Gln Gln Met Tyr Ser Pro Asn Lys Thr Glu Glu Gly Ser Ile Arg
465                 470                 475                 480

Cys Arg Ser Arg Ser Ile Gln Tyr Cys Tyr Leu Gln Glu Asp Ser Ser
                    485                 490                 495

Gln Thr Asn Gly His Ser Ser Ala Ser Pro Ala Ser Gln Arg Cys His
            500                 505                 510
```

-continued

```
Leu Asn Glu Glu Gln Pro Gln His Lys Pro His Gln Cys Lys Cys Lys
        515                 520                 525

Cys Arg Lys Gly Glu Ala Ala Gly Thr Pro Thr Gln Gly Ser Lys Ser
        530                 535                 540

His Ser Asn Lys Gly His Leu Val Leu Met Ser Pro Ala Leu Lys
545                 550                 555                 560

Leu Ala Val Glu Gly Val His Tyr Ile Ala Asp His Leu Arg Ala Glu
                565                 570                 575

Asp Ala Asp Phe Ser Val Lys Glu Asp Trp Lys Tyr Val Ala Met Val
            580                 585                 590

Ile Asp Arg Ile Phe Leu Trp Met Phe Ile Ile Val Cys Leu Leu Gly
        595                 600                 605

Thr Val Gly Leu Phe Leu Pro Pro Trp Leu Ala Gly Met Ile
610                 615                 620
```

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 4
cacgtgccct ccgagctcat ctggcggccg g        31

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 5
gtcatatgtc cacgagccga ac        22

<210> SEQ ID NO 6
<211> LENGTH: 1896
<212> TYPE: DNA
<213> ORGANISM: Artificial Sequence
<220> FEATURE:
<221> NAME/KEY: CDS
<222> LOCATION: (1)..(1893)
<223> OTHER INFORMATION: Description of Artificial Sequence: Modified
      alpha 4 subunit of the chicken nicotinic acetylcholine
      receptor

<400> SEQUENCE: 6

```
atg gga ttt ctc gtg tcg aag gga aac ctc ctc ctc ctg ctg tgt gcc        48
Met Gly Phe Leu Val Ser Lys Gly Asn Leu Leu Leu Leu Leu Cys Ala
1               5                   10                  15 agc atc ttc ccc gct ttc ggc cac gtg gaa acg cga gcc cat gcg gag        96
Ser Ile Phe Pro Ala Phe Gly His Val Glu Thr Arg Ala His Ala Glu
                20                  25                  30 gag cgc ctc ctg aag aaa ctc ttc tcc ggg tat aac aag tgg tcc cgt       144
Glu Arg Leu Leu Lys Lys Leu Phe Ser Gly Tyr Asn Lys Trp Ser Arg
            35                  40                  45 ccc gtc gcc aac att tcg gat gtg gtc ctg gtc cgc ttc ggc ttg tcc       192
Pro Val Ala Asn Ile Ser Asp Val Val Leu Val Arg Phe Gly Leu Ser
        50                  55                  60 ata gcc cag ctc atc gat gtt gat gag aag aac caa atg atg acc aca       240
Ile Ala Gln Leu Ile Asp Val Asp Glu Lys Asn Gln Met Met Thr Thr
65                  70                  75                  80
```

-continued

| | |
|---|---|
| aat gtg tgg gtg aag cag gag tgg cac gac tac aag ctg cgc tgg gac<br>Asn Val Trp Val Lys Gln Glu Trp His Asp Tyr Lys Leu Arg Trp Asp<br>                     85                         90                        95 | 288 |
| ccc cag gag tat gaa aac gtc aca tcc atc cga atc ccc tca gag ctc<br>Pro Gln Glu Tyr Glu Asn Val Thr Ser Ile Arg Ile Pro Ser Glu Leu<br>                   100                    105                 110 | 336 |
| atc tgg agg ccg gac att gtc cta tac aac aat gct gat ggt gac ttt<br>Ile Trp Arg Pro Asp Ile Val Leu Tyr Asn Asn Ala Asp Gly Asp Phe<br>           115                    120                 125 | 384 |
| gca gtc acc cac ctg acc aaa gcc cac ctc ttc tat gat ggg aga att<br>Ala Val Thr His Leu Thr Lys Ala His Leu Phe Tyr Asp Gly Arg Ile<br>130                   135                    140 | 432 |
| aaa tgg atg cca cct gcc atc tac aaa agc tcc tgc agc atc gat gtt<br>Lys Trp Met Pro Pro Ala Ile Tyr Lys Ser Ser Cys Ser Ile Asp Val<br>145                   150                   155                 160 | 480 |
| acc ttc ttc ccc ttt gat cag caa aac tgt aaa atg aaa ttt ggc tct<br>Thr Phe Phe Pro Phe Asp Gln Gln Asn Cys Lys Met Lys Phe Gly Ser<br>                   165                    170                 175 | 528 |
| tgg aca tat gac aaa gct aag ata gac ttg gtg agc atg cat agc cat<br>Trp Thr Tyr Asp Lys Ala Lys Ile Asp Leu Val Ser Met His Ser His<br>                   180                    185                 190 | 576 |
| cgc ggg acc aac gtg gtg gag ctg ggc gtg gac caa ctg gac tac tgg<br>Arg Gly Thr Asn Val Val Glu Leu Gly Val Asp Gln Leu Asp Tyr Trp<br>         195                    200                 205 | 624 |
| gaa agc ggg gag tgg gtc atc att aat gcc gtg ggc aat tac aac agc<br>Glu Ser Gly Glu Trp Val Ile Ile Asn Ala Val Gly Asn Tyr Asn Ser<br>         210                    215                 220 | 672 |
| aag aaa tat gaa tgc tgc aca gag atc tac cct gat ata act tac tcc<br>Lys Lys Tyr Glu Cys Cys Thr Glu Ile Tyr Pro Asp Ile Thr Tyr Ser<br>225                   230                   235                 240 | 720 |
| ttc att atc cgg agg ctg ccg ctg ttc tac aca atc aat ttg atc att<br>Phe Ile Ile Arg Arg Leu Pro Leu Phe Tyr Thr Ile Asn Leu Ile Ile<br>                   245                    250                 255 | 768 |
| ccc tgc ctg ctt atc tcc tgc ttg act gtc ctg gtc ttc tac cta ccc<br>Pro Cys Leu Leu Ile Ser Cys Leu Thr Val Leu Val Phe Tyr Leu Pro<br>                   260                    265                 270 | 816 |
| tct gag tgc gga gag aag ata acc ttg tgc atc tct gtg ctg cta tcc<br>Ser Glu Cys Gly Glu Lys Ile Thr Leu Cys Ile Ser Val Leu Leu Ser<br>         275                    280                 285 | 864 |
| ctc acg gtg ttc ctg ctg ctc atc aca gag atc atc cct tct acc tcc<br>Leu Thr Val Phe Leu Leu Leu Ile Thr Glu Ile Ile Pro Ser Thr Ser<br>         290                    295                 300 | 912 |
| ctg gtc atc ccc ctg ata gga gag tat ctg ctc ttc acc atg ata ttt<br>Leu Val Ile Pro Leu Ile Gly Glu Tyr Leu Leu Phe Thr Met Ile Phe<br>305                   310                   315                 320 | 960 |
| gtc acc ttg tct atc atc atc act gtc ttt gtg ctc aac gta cac cac<br>Val Thr Leu Ser Ile Ile Ile Thr Val Phe Val Leu Asn Val His His<br>                   325                    330                 335 | 1008 |
| cgt tca cca cgt acc cac acg atg cct gac tgg gtg agg agg gtc ttc<br>Arg Ser Pro Arg Thr His Thr Met Pro Asp Trp Val Arg Arg Val Phe<br>         340                    345                 350 | 1056 |
| ctt gac ata gtc cca cgt ctc ctc ttc atg aag cgg ccc tcc aca gtg<br>Leu Asp Ile Val Pro Arg Leu Leu Phe Met Lys Arg Pro Ser Thr Val<br>           355                    360                 365 | 1104 |
| aaa gac aat tgc aag aag ctt att gaa tct atg cac aaa cta acc aac<br>Lys Asp Asn Cys Lys Lys Leu Ile Glu Ser Met His Lys Leu Thr Asn<br>         370                    375                 380 | 1152 |
| tca cca agg ctt tgg tct gag acc gac atg gag ccc aac ttc act acc<br>Ser Pro Arg Leu Trp Ser Glu Thr Asp Met Glu Pro Asn Phe Thr Thr<br>385                   390                   395                 400 | 1200 |

-continued

```
tca tcc tcc ccc agc ccc cag agt aat gaa cct tca ccc aca tct tcc      1248
Ser Ser Ser Pro Ser Pro Gln Ser Asn Glu Pro Ser Pro Thr Ser Ser
            405                 410                 415 ttc tgt gcc cac ctt gag gag cca gcc aaa cct atg tgc aaa tcc cct      1296
Phe Cys Ala His Leu Glu Glu Pro Ala Lys Pro Met Cys Lys Ser Pro
            420                 425                 430 tct gga cag tac tca atg ctg cac cct gag ccc cca cag gtg acg tgt      1344
Ser Gly Gln Tyr Ser Met Leu His Pro Glu Pro Pro Gln Val Thr Cys
            435                 440                 445 tcc tct ccg aag ccc tcc tgc cac ccc ctg agt gac acc cag acc aca      1392
Ser Ser Pro Lys Pro Ser Cys His Pro Leu Ser Asp Thr Gln Thr Thr
450                 455                 460 tct atc tca aaa ggc aga tcg ctc agt gtt cag cag atg tac agc ccc      1440
Ser Ile Ser Lys Gly Arg Ser Leu Ser Val Gln Gln Met Tyr Ser Pro
465                 470                 475                 480 aat aag aca gag gaa ggg agc atc cgc tgt agg tcc cga agc atc cag      1488
Asn Lys Thr Glu Glu Gly Ser Ile Arg Cys Arg Ser Arg Ser Ile Gln
            485                 490                 495 tac tgt tac ctg cag gag gac tct tcc cag acc aat ggc cac tct agt      1536
Tyr Cys Tyr Leu Gln Glu Asp Ser Ser Gln Thr Asn Gly His Ser Ser
            500                 505                 510 gcc tct cca gcg tcg cag cgc tgc cac ctc aat gaa gag cag ccc cag      1584
Ala Ser Pro Ala Ser Gln Arg Cys His Leu Asn Glu Glu Gln Pro Gln
            515                 520                 525 cac aag ccc cac cag tgc aag tgt aag tgc aga aag gga gag gca gct      1632
His Lys Pro His Gln Cys Lys Cys Lys Cys Arg Lys Gly Glu Ala Ala
            530                 535                 540 ggc aca ccg act caa gga agc aag agc cac agc aac aaa gga gaa cac      1680
Gly Thr Pro Thr Gln Gly Ser Lys Ser His Ser Asn Lys Gly Glu His
545                 550                 555                 560 ctc gtg ctg atg tcc cca gcc ctg aag ctg gcg gtg gaa ggg gtc cac      1728
Leu Val Leu Met Ser Pro Ala Leu Lys Leu Ala Val Glu Gly Val His
            565                 570                 575 tac att gca gac cac ctg cga gca gaa gat gca gat ttc tca gtg aag      1776
Tyr Ile Ala Asp His Leu Arg Ala Glu Asp Ala Asp Phe Ser Val Lys
            580                 585                 590 gaa gac tgg aag tac gta gca atg gtc att gac cgg atc ttt ctc tgg      1824
Glu Asp Trp Lys Tyr Val Ala Met Val Ile Asp Arg Ile Phe Leu Trp
            595                 600                 605 atg ttc atc atc gtg tgt ttg ctg ggg acc gtt ggg ctc ttc ctc ccg      1872
Met Phe Ile Ile Val Cys Leu Leu Gly Thr Val Gly Leu Phe Leu Pro
            610                 615                 620 ccg tgg ctg gca gga atg atc taa                                      1896
Pro Trp Leu Ala Gly Met Ile
625                 630
```

<210> SEQ ID NO 7
<211> LENGTH: 631
<212> TYPE: PRT
<213> ORGANISM: Artificial Sequence
<220> FEATURE:
<223> OTHER INFORMATION: Description of Artificial Sequence: Modified
      alpha 4 subunit of the chicken nicotinic acetylcholine
      receptor

<400> SEQUENCE: 7

```
Met Gly Phe Leu Val Ser Lys Gly Asn Leu Leu Leu Leu Leu Cys Ala
1               5                   10                  15

Ser Ile Phe Pro Ala Phe Gly His Val Glu Thr Arg Ala His Ala Glu
            20                  25                  30
```

-continued

```
Glu Arg Leu Leu Lys Lys Leu Phe Ser Gly Tyr Asn Lys Trp Ser Arg
         35                  40                  45
Pro Val Ala Asn Ile Ser Asp Val Leu Val Arg Phe Gly Leu Ser
 50                  55                  60
Ile Ala Gln Leu Ile Asp Val Asp Glu Lys Asn Gln Met Met Thr Thr
 65                  70                  75                  80
Asn Val Trp Val Lys Gln Glu Trp His Asp Tyr Lys Leu Arg Trp Asp
                 85                  90                  95
Pro Gln Glu Tyr Glu Asn Val Thr Ser Ile Arg Ile Pro Ser Glu Leu
                100                 105                 110
Ile Trp Arg Pro Asp Ile Val Leu Tyr Asn Asn Ala Asp Gly Asp Phe
             115                 120                 125
Ala Val Thr His Leu Thr Lys Ala His Leu Phe Tyr Asp Gly Arg Ile
130                 135                 140
Lys Trp Met Pro Pro Ala Ile Tyr Lys Ser Ser Cys Ser Ile Asp Val
145                 150                 155                 160
Thr Phe Phe Pro Phe Asp Gln Gln Asn Cys Lys Met Lys Phe Gly Ser
                165                 170                 175
Trp Thr Tyr Asp Lys Ala Lys Ile Asp Leu Val Ser Met His Ser His
            180                 185                 190
Arg Gly Thr Asn Val Val Glu Leu Gly Val Asp Gln Leu Asp Tyr Trp
        195                 200                 205
Glu Ser Gly Glu Trp Val Ile Ile Asn Ala Val Gly Asn Tyr Asn Ser
    210                 215                 220
Lys Lys Tyr Glu Cys Cys Thr Glu Ile Tyr Pro Asp Ile Thr Tyr Ser
225                 230                 235                 240
Phe Ile Ile Arg Arg Leu Pro Leu Phe Tyr Thr Ile Asn Leu Ile Ile
                245                 250                 255
Pro Cys Leu Leu Ile Ser Cys Leu Thr Val Leu Val Phe Tyr Leu Pro
            260                 265                 270
Ser Glu Cys Gly Glu Lys Ile Thr Leu Cys Ile Ser Val Leu Leu Ser
        275                 280                 285
Leu Thr Val Phe Leu Leu Ile Thr Glu Ile Ile Pro Ser Thr Ser
    290                 295                 300
Leu Val Ile Pro Leu Ile Gly Glu Tyr Leu Leu Phe Thr Met Ile Phe
305                 310                 315                 320
Val Thr Leu Ser Ile Ile Ile Thr Val Phe Val Leu Asn Val His His
                325                 330                 335
Arg Ser Pro Arg Thr His Thr Met Pro Asp Trp Val Arg Arg Val Phe
            340                 345                 350
Leu Asp Ile Val Pro Arg Leu Leu Phe Met Lys Arg Pro Ser Thr Val
        355                 360                 365
Lys Asp Asn Cys Lys Lys Leu Ile Glu Ser Met His Lys Leu Thr Asn
370                 375                 380
Ser Pro Arg Leu Trp Ser Glu Thr Asp Met Glu Pro Asn Phe Thr Thr
385                 390                 395                 400
Ser Ser Ser Pro Ser Pro Gln Ser Asn Glu Pro Ser Pro Thr Ser Ser
                405                 410                 415
Phe Cys Ala His Leu Glu Glu Pro Ala Lys Pro Met Cys Lys Ser Pro
            420                 425                 430
Ser Gly Gln Tyr Ser Met Leu His Pro Glu Pro Pro Gln Val Thr Cys
        435                 440                 445
Ser Ser Pro Lys Pro Ser Cys His Pro Leu Ser Asp Thr Gln Thr Thr
```

```
                450               455               460
Ser Ile Ser Lys Gly Arg Ser Leu Ser Val Gln Gln Met Tyr Ser Pro
465               470                       475                     480

Asn Lys Thr Glu Glu Gly Ser Ile Arg Cys Arg Ser Arg Ser Ile Gln
                        485                       490                     495

Tyr Cys Tyr Leu Gln Glu Asp Ser Ser Gln Thr Asn Gly His Ser Ser
                500                     505                     510

Ala Ser Pro Ala Ser Gln Arg Cys His Leu Asn Glu Glu Gln Pro Gln
            515                     520                     525

His Lys Pro His Gln Cys Lys Cys Lys Cys Arg Lys Gly Glu Ala Ala
530                     535                     540

Gly Thr Pro Thr Gln Gly Ser Lys Ser His Ser Asn Lys Gly Glu His
545                     550                     555                     560

Leu Val Leu Met Ser Pro Ala Leu Lys Leu Ala Val Glu Gly Val His
                565                     570                     575

Tyr Ile Ala Asp His Leu Arg Ala Glu Asp Ala Asp Phe Ser Val Lys
                580                     585                     590

Glu Asp Trp Lys Tyr Val Ala Met Val Ile Asp Arg Ile Phe Leu Trp
            595                     600                     605

Met Phe Ile Ile Val Cys Leu Leu Gly Thr Val Gly Leu Phe Leu Pro
    610                     615                     620

Pro Trp Leu Ala Gly Met Ile
625               630

<210> SEQ ID NO 8
<211> LENGTH: 81
<212> TYPE: DNA
<213> ORGANISM: Artificial Sequence
<220> FEATURE:
<223> OTHER INFORMATION: Description of Artificial Sequence: Primer

<400> SEQUENCE: 8
gctaagatag acttgagaca catcgatgag gctagaggaa ccaacgtggt agaactgggt    60
gtggaccaac tggactactg g                                              81

<210> SEQ ID NO 9
<211> LENGTH: 81
<212> TYPE: DNA
<213> ORGANISM: Artificial Sequence
<220> FEATURE:
<223> OTHER INFORMATION: Description of Artificial Sequence: Primer

<400> SEQUENCE: 9
ccagtagtcc agttggtcca cacccagttc taccacgttg gttcctctag cctcatcgat    60
gtgtctcaag tctatcttag c                                              81

<210> SEQ ID NO 10
<211> LENGTH: 1869
<212> TYPE: DNA
<213> ORGANISM: Artificial Sequence
<220> FEATURE:
<221> NAME/KEY: CDS
<222> LOCATION: (1)..(1866)
<223> OTHER INFORMATION: Description of Artificial Sequence: Modified
      alpha 4 subunit of the chicken nicotinic acetylcholine
      receptor

<400> SEQUENCE: 10 atg gga ttt ctc gtg tcg aag gga aac ctc ctc ctc ctg ctg tgt gcc    48
Met Gly Phe Leu Val Ser Lys Gly Asn Leu Leu Leu Leu Leu Cys Ala
```

-continued

| | | | | |
|---|---|---|---|---|
| 1 | 5 | 10 | 15 | |

| | | |
|---|---|---|
| agc atc ttc ccc gct ttc ggc cac gtg aaa acg cga gcc cat gcg gag<br>Ser Ile Phe Pro Ala Phe Gly His Val Glu Thr Arg Ala His Ala Glu<br>20 25 30 | 96 | |
| gag cgc ctg ctg aag aaa ctc ttc tcc ggg tat aac aag tgg tcc cgt<br>Glu Arg Leu Leu Lys Lys Leu Phe Ser Gly Tyr Asn Lys Trp Ser Arg<br>35 40 45 | 144 | |
| ccc gtc gcc aac att tcg gat gtg gtc ctg gtc cgc ttc ggc ttg tcc<br>Pro Val Ala Asn Ile Ser Asp Val Val Leu Val Arg Phe Gly Leu Ser<br>50 55 60 | 192 | |
| ata gcc cag ctc atc gat gtt gat gag aag aac caa atg atg acc aca<br>Ile Ala Gln Leu Ile Asp Val Asp Glu Lys Asn Gln Met Met Thr Thr<br>65 70 75 80 | 240 | |
| aat gtg tgg gtg aag cag gag tgg cac gac tac aag ctg cgc tgg gac<br>Asn Val Trp Val Lys Gln Glu Trp His Asp Tyr Lys Leu Arg Trp Asp<br>85 90 95 | 288 | |
| ccc cag gag tat gaa aac gtc aca tcc atc cga atc ccc tca gag ctc<br>Pro Gln Glu Tyr Glu Asn Val Thr Ser Ile Arg Ile Pro Ser Glu Leu<br>100 105 110 | 336 | |
| atc tgg agg ccg gac att gtc cta tac aac aat gct gat ggt gac ttt<br>Ile Trp Arg Pro Asp Ile Val Leu Tyr Asn Asn Ala Asp Gly Asp Phe<br>115 120 125 | 384 | |
| gca gtc acc cac ctg acc aaa gcc cac ctc ttc tat gat ggg aga att<br>Ala Val Thr His Leu Thr Lys Ala His Leu Phe Tyr Asp Gly Arg Ile<br>130 135 140 | 432 | |
| aaa tgg atg cca cct gcc atc tac aaa agc tcc tgc agc atc gat gtt<br>Lys Trp Met Pro Pro Ala Ile Tyr Lys Ser Ser Cys Ser Ile Asp Val<br>145 150 155 160 | 480 | |
| acc ttc ttc ccc ttt gat cag caa aac tgt aaa atg aaa ttt ggc tct<br>Thr Phe Phe Pro Phe Asp Gln Gln Asn Cys Lys Met Lys Phe Gly Ser<br>165 170 175 | 528 | |
| tgg aca tat gac aaa gct aag ata gac ttg gtg agc atg cat agc cat<br>Trp Thr Tyr Asp Lys Ala Lys Ile Asp Leu Val Ser Met His Ser His<br>180 185 190 | 576 | |
| gtc gac ctg tcc gag ttc tac acc tcc gtg gag tgg gac atc ctg gag<br>Val Asp Leu Ser Glu Phe Tyr Thr Ser Val Glu Trp Asp Ile Leu Glu<br>195 200 205 | 624 | |
| gtg cca gcc gtc agg aac gag aag ttc tac acg tgc tgc gac gag ccc<br>Val Pro Ala Val Arg Asn Glu Lys Phe Tyr Thr Cys Cys Asp Glu Pro<br>210 215 220 | 672 | |
| tac ctg gac ata acg ttt aac ttc att atc cgg agg ctg ccg ctg ttc<br>Tyr Leu Asp Ile Thr Phe Asn Phe Ile Ile Arg Arg Leu Pro Leu Phe<br>225 230 235 240 | 720 | |
| tac aca atc aat ttg atc att ccc tgc ctg ctt atc tcc tgc ttg act<br>Tyr Thr Ile Asn Leu Ile Ile Pro Cys Leu Leu Ile Ser Cys Leu Thr<br>245 250 255 | 768 | |
| gtc ctg gtc ttc tac cta ccc tct gag tgc gga gag aag ata acc ttg<br>Val Leu Val Phe Tyr Leu Pro Ser Glu Cys Gly Glu Lys Ile Thr Leu<br>260 265 270 | 816 | |
| tgc atc tct gtg ctg cta tcc ctc acg gtg ttc ctg ctc atc aca<br>Cys Ile Ser Val Leu Leu Ser Leu Thr Val Phe Leu Leu Ile Thr<br>275 280 285 | 864 | |
| gag atc atc cct tct acc tcc ctg gtc atc ccc ctg ata gga gag tat<br>Glu Ile Ile Pro Ser Thr Ser Leu Val Ile Pro Leu Ile Gly Glu Tyr<br>290 295 300 | 912 | |
| ctg ctc ttc acc atg ata ttt gtc acc ttg tct atc atc atc act gtc<br>Leu Leu Phe Thr Met Ile Phe Val Thr Leu Ser Ile Ile Ile Thr Val<br>305 310 315 320 | 960 | |
| ttt gtg ctc aac gta cac cac cgt tca cca cgt acc cac acg atg cct | 1008 | |

-continued

```
Phe Val Leu Asn Val His His Arg Ser Pro Arg Thr His Thr Met Pro
            325                 330                 335 gac tgg gtg agg agg gtc ttc ctt gac ata gtc cca cgt ctc ctc ttc      1056
Asp Trp Val Arg Arg Val Phe Leu Asp Ile Val Pro Arg Leu Leu Phe
            340                 345                 350 atg aag cgg ccc tcc aca gtg aaa gac aat tgc aag aag ctt att gaa      1104
Met Lys Arg Pro Ser Thr Val Lys Asp Asn Cys Lys Lys Leu Ile Glu
            355                 360                 365 tct atg cac aaa cta acc aac tca cca agg ctt tgg tct gag acc gac      1152
Ser Met His Lys Leu Thr Asn Ser Pro Arg Leu Trp Ser Glu Thr Asp
            370                 375                 380 atg gag ccc aac ttc act acc tca tcc tcc ccc agc ccc cag agt aat      1200
Met Glu Pro Asn Phe Thr Thr Ser Ser Ser Pro Ser Pro Gln Ser Asn
385                 390                 395                 400 gaa cct tca ccc aca tct tcc ttc tgt gcc cac ctt gag gag cca gcc      1248
Glu Pro Ser Pro Thr Ser Ser Phe Cys Ala His Leu Glu Glu Pro Ala
                405                 410                 415 aaa cct atg tgc aaa tcc cct tct gga cag tac tca atg ctg cac cct      1296
Lys Pro Met Cys Lys Ser Pro Ser Gly Gln Tyr Ser Met Leu His Pro
            420                 425                 430 gag ccc cca cag gtg acg tgt tcc tct ccg aag ccc tcc tgc cac ccc      1344
Glu Pro Pro Gln Val Thr Cys Ser Ser Pro Lys Pro Ser Cys His Pro
            435                 440                 445 ctg agt gac acc cag acc aca tct atc tca aaa ggc aga tcg ctc agt      1392
Leu Ser Asp Thr Gln Thr Thr Ser Ile Ser Lys Gly Arg Ser Leu Ser
            450                 455                 460 gtt cag cag atg tac agc ccc aat aag aca gag gaa ggg agc atc cgc      1440
Val Gln Gln Met Tyr Ser Pro Asn Lys Thr Glu Glu Gly Ser Ile Arg
465                 470                 475                 480 tgt agg tcc cga agc atc cag tac tgt tac ctg cag gag gac tct tcc      1488
Cys Arg Ser Arg Ser Ile Gln Tyr Cys Tyr Leu Gln Glu Asp Ser Ser
                485                 490                 495 cag acc aat ggc cac tct agt gcc tct cca gcg tcg cag cgc tgc cac      1536
Gln Thr Asn Gly His Ser Ser Ala Ser Pro Ala Ser Gln Arg Cys His
            500                 505                 510 ctc aat gaa gag cag ccc cag cac aag ccc cac cag tgc aag tgt aag      1584
Leu Asn Glu Glu Gln Pro Gln His Lys Pro His Gln Cys Lys Cys Lys
            515                 520                 525 tgc aga aag gga gag gca gct ggc aca ccg act caa gga agc aag agc      1632
Cys Arg Lys Gly Glu Ala Ala Gly Thr Pro Thr Gln Gly Ser Lys Ser
            530                 535                 540 cac agc aac aaa gga gaa cac ctc gtg ctg atg tcc cca gcc ctg aag      1680
His Ser Asn Lys Gly Glu His Leu Val Leu Met Ser Pro Ala Leu Lys
545                 550                 555                 560 ctg gcg gtg gaa ggg gtc cac tac att gca gac cac ctg cga gca gaa      1728
Leu Ala Val Glu Gly Val His Tyr Ile Ala Asp His Leu Arg Ala Glu
                565                 570                 575 gat gca gat ttc tca gtg aag gaa gac tgg aag tac gta gca atg gtc      1776
Asp Ala Asp Phe Ser Val Lys Glu Asp Trp Lys Tyr Val Ala Met Val
            580                 585                 590 att gac cgg atc ttt ctc tgg atg ttc atc atc gtg tgt ttg ctg ggg      1824
Ile Asp Arg Ile Phe Leu Trp Met Phe Ile Ile Val Cys Leu Leu Gly
            595                 600                 605 acc gtt ggg ctc ttc ctc ccg ccg tgg ctg gca gga atg atc taa          1869
Thr Val Gly Leu Phe Leu Pro Pro Trp Leu Ala Gly Met Ile
            610                 615                 620

<210> SEQ ID NO 11
<211> LENGTH: 622
<212> TYPE: PRT
```

<213> ORGANISM: Artificial Sequence
<220> FEATURE:
<223> OTHER INFORMATION: Description of Artificial Sequence: Modified alpha 4 subunit of the chicken nicotinic acetylcholine receptor

<400> SEQUENCE: 11

```
Met Gly Phe Leu Val Ser Lys Gly Asn Leu Leu Leu Leu Leu Cys Ala
  1               5                  10                  15

Ser Ile Phe Pro Ala Phe Gly His Val Glu Thr Arg Ala His Ala Glu
             20                  25                  30

Glu Arg Leu Leu Lys Lys Leu Phe Ser Gly Tyr Asn Lys Trp Ser Arg
         35                  40                  45

Pro Val Ala Asn Ile Ser Asp Val Val Leu Val Arg Phe Gly Leu Ser
     50                  55                  60

Ile Ala Gln Leu Ile Asp Val Asp Glu Lys Asn Gln Met Met Thr Thr
 65                  70                  75                  80

Asn Val Trp Val Lys Gln Glu Trp His Asp Tyr Lys Leu Arg Trp Asp
                 85                  90                  95

Pro Gln Glu Tyr Glu Asn Val Thr Ser Ile Arg Ile Pro Ser Glu Leu
            100                 105                 110

Ile Trp Arg Pro Asp Ile Val Leu Tyr Asn Asn Ala Asp Gly Asp Phe
        115                 120                 125

Ala Val Thr His Leu Thr Lys Ala His Leu Phe Tyr Asp Gly Arg Ile
    130                 135                 140

Lys Trp Met Pro Pro Ala Ile Tyr Lys Ser Ser Cys Ser Ile Asp Val
145                 150                 155                 160

Thr Phe Phe Pro Phe Asp Gln Gln Asn Cys Lys Met Lys Phe Gly Ser
                165                 170                 175

Trp Thr Tyr Asp Lys Ala Lys Ile Asp Leu Val Ser Met His Ser His
            180                 185                 190

Val Asp Leu Ser Glu Phe Tyr Thr Ser Val Glu Trp Asp Ile Leu Glu
        195                 200                 205

Val Pro Ala Val Arg Asn Glu Lys Phe Tyr Thr Cys Cys Asp Glu Pro
    210                 215                 220

Tyr Leu Asp Ile Thr Phe Asn Phe Ile Ile Arg Arg Leu Pro Leu Phe
225                 230                 235                 240

Tyr Thr Ile Asn Leu Ile Ile Pro Cys Leu Leu Ile Ser Cys Leu Thr
                245                 250                 255

Val Leu Val Phe Tyr Leu Pro Ser Glu Cys Gly Glu Lys Ile Thr Leu
            260                 265                 270

Cys Ile Ser Val Leu Leu Ser Leu Thr Val Phe Leu Leu Leu Ile Thr
        275                 280                 285

Glu Ile Ile Pro Ser Thr Ser Leu Val Ile Pro Leu Ile Gly Glu Tyr
    290                 295                 300

Leu Leu Phe Thr Met Ile Phe Val Thr Leu Ser Ile Ile Ile Thr Val
305                 310                 315                 320

Phe Val Leu Asn Val His His Arg Ser Pro Arg Thr His Thr Met Pro
                325                 330                 335

Asp Trp Val Arg Arg Val Phe Leu Asp Ile Val Pro Arg Leu Leu Phe
            340                 345                 350

Met Lys Arg Pro Ser Thr Val Lys Asp Asn Cys Lys Lys Leu Ile Glu
        355                 360                 365

Ser Met His Lys Leu Thr Asn Ser Pro Arg Leu Trp Ser Glu Thr Asp
    370                 375                 380
```

```
Met Glu Pro Asn Phe Thr Thr Ser Ser Pro Ser Gln Ser Asn
385                 390                 395                 400

Glu Pro Ser Pro Thr Ser Ser Phe Cys Ala His Leu Glu Glu Pro Ala
                405                 410                 415

Lys Pro Met Cys Lys Ser Pro Ser Gly Gln Tyr Ser Met Leu His Pro
            420                 425                 430

Glu Pro Pro Gln Val Thr Cys Ser Ser Pro Lys Pro Ser Cys His Pro
        435                 440                 445

Leu Ser Asp Thr Gln Thr Thr Ser Ile Ser Lys Gly Arg Ser Leu Ser
    450                 455                 460

Val Gln Gln Met Tyr Ser Pro Asn Lys Thr Glu Glu Gly Ser Ile Arg
465                 470                 475                 480

Cys Arg Ser Arg Ser Ile Gln Tyr Cys Tyr Leu Gln Glu Asp Ser Ser
                485                 490                 495

Gln Thr Asn Gly His Ser Ser Ala Ser Pro Ala Ser Gln Arg Cys His
            500                 505                 510

Leu Asn Glu Glu Gln Pro Gln His Lys Pro His Gln Cys Lys Cys Lys
        515                 520                 525

Cys Arg Lys Gly Glu Ala Ala Gly Thr Pro Thr Gln Gly Ser Lys Ser
    530                 535                 540

His Ser Asn Lys Gly Glu His Leu Val Leu Met Ser Pro Ala Leu Lys
545                 550                 555                 560

Leu Ala Val Glu Gly Val His Tyr Ile Ala Asp His Leu Arg Ala Glu
                565                 570                 575

Asp Ala Asp Phe Ser Val Lys Glu Asp Trp Lys Tyr Val Ala Met Val
            580                 585                 590

Ile Asp Arg Ile Phe Leu Trp Met Phe Ile Val Cys Leu Leu Gly
        595                 600                 605

Thr Val Gly Leu Phe Leu Pro Pro Trp Leu Ala Gly Met Ile
    610                 615                 620

<210> SEQ ID NO 12
<211> LENGTH: 79
<212> TYPE: DNA
<213> ORGANISM: Artificial Sequence
<220> FEATURE:
<223> OTHER INFORMATION: Description of Artificial Sequence: Primer

<400> SEQUENCE: 12
caacagcaag aaatatgaat gctgcgacga gccctacctt gatataactt tcaacttcat    60
tatccggagg ctgccgctg                                                  79

<210> SEQ ID NO 13
<211> LENGTH: 79
<212> TYPE: DNA
<213> ORGANISM: Artificial Sequence
<220> FEATURE:
<223> OTHER INFORMATION: Description of Artificial Sequence: Primer

<400> SEQUENCE: 13
cagcggcagc ctccggataa tgaagttgaa agttatatca aggtagggct cgtcgcagca    60
ttcatatttc ttgctgttg                                                  79

<210> SEQ ID NO 14
<211> LENGTH: 30
<212> TYPE: DNA
<213> ORGANISM: Artificial Sequence
```

-continued

```
<220> FEATURE:
<223> OTHER INFORMATION: Description of Artificial Sequence: Primer

<400> SEQUENCE: 14
gaacaaaagc tggaggtcca ccgcggtggc                                   30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 15
gccaccgcgg tggacctcca gcttttgttc                                   30

<210> SEQ ID NO 16
<211> LENGTH: 75
<212> TYPE: DNA
<213> ORGANISM: Artificial Sequence
<220> FEATURE:
<223> OTHER INFORMATION: Description of Artificial Sequence: Primer

<400> SEQUENCE: 16
gcggggagtg ggtcatctta gaagtcccgg ccgttcgcaa cgaaaagttt tatacatgct  60
gcgacgagcc ctacc                                                   75

<210> SEQ ID NO 17
<211> LENGTH: 75
<212> TYPE: DNA
<213> ORGANISM: Artificial Sequence
<220> FEATURE:
<223> OTHER INFORMATION: Description of Artificial Sequence: Primer

<400> SEQUENCE: 17
ggtagggctc gtcgcagcat gtataaaact tttcgttgcg aacggccggg acttcaatga  60
tgacccactc cccgc                                                   75
```